(12) United States Patent
Shaw et al.

(10) Patent No.: US 9,926,270 B2
(45) Date of Patent: Mar. 27, 2018

(54) PROCESS FOR PRODUCTION OF GLYCOPYRRONIUM TOSYLATE

(71) Applicant: Dermira, Inc., Redwood City, CA (US)

(72) Inventors: Anthony Adrian Shaw, Redwood City, CA (US); Enrico Vigano, Milan (IT); Renato Molteni, Milan (IT)

(73) Assignee: DERMIRA, INC., Redwood City, CA (US)

( * ) Notice: Subject to any disclaimer, the term of this patent is extended or adjusted under 35 U.S.C. 154(b) by 0 days.

(21) Appl. No.: 14/830,638

(22) Filed: Aug. 19, 2015

(65) Prior Publication Data
US 2016/0052879 A1    Feb. 25, 2016

Related U.S. Application Data

(60) Provisional application No. 62/039,811, filed on Aug. 20, 2014.

(51) Int. Cl.

| C07D 207/12 | (2006.01) |
|---|---|
| C07C 309/73 | (2006.01) |
| C07C 303/22 | (2006.01) |
| C07C 201/12 | (2006.01) |
| C07C 309/30 | (2006.01) |

(52) U.S. Cl.
CPC .......... *C07D 207/12* (2013.01); *C07C 201/12* (2013.01); *C07C 303/22* (2013.01); *C07C 309/30* (2013.01); *C07C 309/73* (2013.01)

(58) Field of Classification Search
CPC .................................................. C07D 207/12
See application file for complete search history.

(56) References Cited

U.S. PATENT DOCUMENTS

| 2,956,062 | A | * | 10/1960 | Lunsford | ............. | C07D 207/12 |
|---|---|---|---|---|---|---|
| | | | | | | 548/556 |
| 5,183,811 | A | * | 2/1993 | Masaki | ............. | C07F 9/10 |
| | | | | | | 514/79 |
| 5,525,347 | A | | 6/1996 | Kellner et al. | | |
| 5,919,760 | A | | 7/1999 | Simon | | |
| 6,063,808 | A | | 5/2000 | Fabiano et al. | | |
| 6,204,285 | B1 | | 3/2001 | Fabiano et al. | | |
| 6,214,792 | B1 | | 4/2001 | Simon | | |
| 6,307,060 | B1 | | 10/2001 | Noe et al. | | |
| 6,613,795 | B2 | | 9/2003 | Noe et al. | | |
| 7,253,182 | B2 | | 8/2007 | Noe et al. | | |
| 8,558,008 | B2 | * | 10/2013 | Statler | ............. | C07D 207/12 |
| | | | | | | 548/556 |
| 8,859,610 | B2 | * | 10/2014 | Statler | ............. | C07D 207/12 |
| | | | | | | 514/424 |
| 9,006,461 | B2 | * | 4/2015 | Statler | ............. | C07D 207/12 |
| | | | | | | 548/556 |
| 9,006,462 | B2 | * | 4/2015 | Statler | ............. | A61L 15/24 |
| | | | | | | 548/556 |
| 9,259,414 | B2 | * | 2/2016 | Statler | ............. | A61L 15/24 |
| 2004/0142844 | A1 | * | 7/2004 | Miracle | ............. | C07C 255/25 |
| | | | | | | 510/376 |
| 2008/0227988 | A1 | | 9/2008 | Baxter et al. | | |
| 2008/0292562 | A1 | | 11/2008 | Pieper et al. | | |
| 2009/0005577 | A1 | | 1/2009 | Kraiouchkine | | |
| 2010/0276329 | A1 | | 11/2010 | Johnston et al. | | |
| 2011/0305645 | A1 | | 12/2011 | Pivetti et al. | | |
| 2011/0306650 | A1 | * | 12/2011 | Pivetti | ............. | A61K 31/40 |
| | | | | | | 514/424 |
| 2012/0022127 | A1 | | 1/2012 | Allmendinger | | |
| 2013/0211101 | A1 | * | 8/2013 | Statler | ............. | C07C 309/30 |
| | | | | | | 548/556 |

FOREIGN PATENT DOCUMENTS

| FI | 49713 | | 6/1975 | | |
|---|---|---|---|---|---|
| WO | 2010115937 | A1 | † | 10/2010 | |
| WO | WO2010/115937 | A1 | | 10/2010 | |
| WO | WO 2014134510 | A1 | * | 9/2014 | ........... C07D 207/12 |

OTHER PUBLICATIONS

Calogeropoulou et al., "Design and Synthesis of Potent antileishmanial Cycloalkylidene-Substituted Ether Phospholipid Derivatives", vol. 51, p. 897-908 (2008) J. Med. Chem.

Lukac et al., Dialklyamino and Nitrogen Heterocyclic Analogues of Hexadecylphosphocholine and Cetyltrimethylammonium Bromide: Effect of Phosphate Group and Environment of the Ammonium Cation on their Biological Activity, vol. 44, p. 4970-4977, (2009) Eur. J. Med. Chem.†

Calogeropoulou et al., "Design and Synthesis of Potent antileishmanial Cycloalkylidene-Substituted Ether Phospholipid Derivatives,", vol. 51, p. 897-908 (2008) J. Med. Chem.†

\* cited by examiner
† cited by third party

*Primary Examiner* — Matthew P Coughlin
(74) *Attorney, Agent, or Firm* — Squire Patton Boggs (US) LLP

(57) ABSTRACT

Provided herein are methods for the production of glycopyrronium tosylate and glycopyrronium tosylate compositions. Also provided herein are compositions useful in the production of glycopyrronium tosylate. Additionally provided herein are glycopyrronium tosylate compositions. Glycopyrronium tosylate is useful for the treatment of, among other conditions, hyperhidrosis.

29 Claims, No Drawings

PROCESS FOR PRODUCTION OF GLYCOPYRRONIUM TOSYLATE

CROSS-REFERENCE TO RELATED APPLICATION

This application claims benefit of, and priority to under 35 U.S.C. § 119(e), U.S. Provisional Application Ser. No. 62/039,811, entitled "PROCESS FOR PRODUCTION OF GLYCOPYRRONIUM TOSYLATE," filed on Aug. 20, 2014, which is incorporated by reference herein in its entirety.

FIELD

Provided herein are methods for the production of glycopyrronium tosylate. Also provided herein are compositions useful in the production of glycopyrronium tosylate. Glycopyrronium tosylate is useful for the treatment of, among other conditions, hyperhidrosis.

BACKGROUND

Glycopyrrolate is a salt of quaternary ammonium cation of the muscarinic anticholinergic group. Glycopyrrolate, typically as a bromide salt, has been described for the treatment of a variety of conditions including diarrhea (U.S. Pat. No. 6,214,792 B1 and U.S. Pat. No. 5,919,760 A), urinary incontinence (U.S. Pat. No. 6,204,285 B1 and U.S. Pat. No. 6,063,808 A), and anxiety (U.S. Pat. No. 5,525,347 A). Glycopyrrolate has also been described for the treatment of hyperhidrosis in U.S. Pat. Appl. No. US 2010/0276329 A1.

Glycopyrrolate has been made available as a bromide salt or an acetate salt. The bromide salt of glycopyrrolate is sold as Rubinol®. The term "glycopyrrolate" as used in the label for Rubinol® refers to the bromide salt, also more formally referred to as glycopyrronium bromide. Glycopyrronium tosylate has been described in U.S. Pat. No. 8,558,008 B2. Glycopyrrolate used pharmaceutically is the racemic threo form.

Glycopyrronium bromide is commercially available and the synthesis has been described in U.S. Pat. No. 2,956,062 and in Finnish Pat. No. 49,713. Several routes for the production of glycopyrronium tosylate have been described in U.S. Pat. No. 8,558,008 B2.

SUMMARY

Provided herein are methods of producing glycopyrronium tosylate useful, for example, for the treatment of hyperhidrosis. Also provided herein are compositions useful in the preparation of glycopyrronium tosylate.

In certain embodiments, methods of producing glycopyrronium tosylate described herein comprise the use of methyl tosylate as a methylating agent. Prior methods for the production of glycopyrronium bromide described the use of methylbromide as a methylating agent. See, Finnish Pat. No. 49,713. Prior methods of production of glycopyrronium tosylate described exchange of glycopyrronium acetate and p-toluenesulfonic acid, or exchange of glycopyrronium bromide and silver tosylate. See, U.S. Pat. No. 8,558,008 B2. The methods described herein provide a novel method to produce glycopyrronium tosylate by the use of methyl tosylate as a methylating agent. This novel method comprises fewer steps and results in enhanced stereochemical selection with respect to prior methods to produce glycopyrronium tosylate. Furthermore, incomplete anion exchange and silver contamination associated with previously described methods are avoided. Avoidance of the use of expensive silver salts renders the large scale manufacture of glycopyrronium tosylate economically more viable and environmentally more sound using the method described herein.

In an aspect, provided herein are methods of producing glycopyrronium tosylate comprising contacting glycopyrrolate base with methyl tosylate to produce glycopyrronium tosylate:

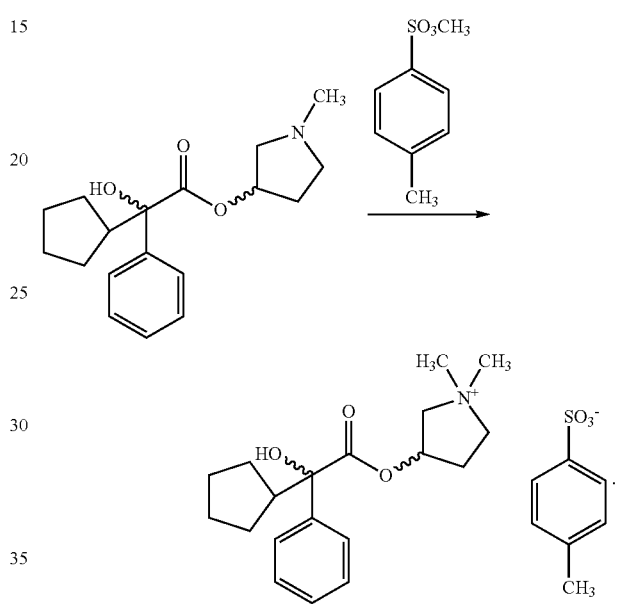

In an embodiment, provided herein are methods of producing glycopyrronium tosylate comprising:

(i) contacting cyclopentylmandelic acid with 1-methylpyrrolidin-3-ol to form glycopyrrolate base:

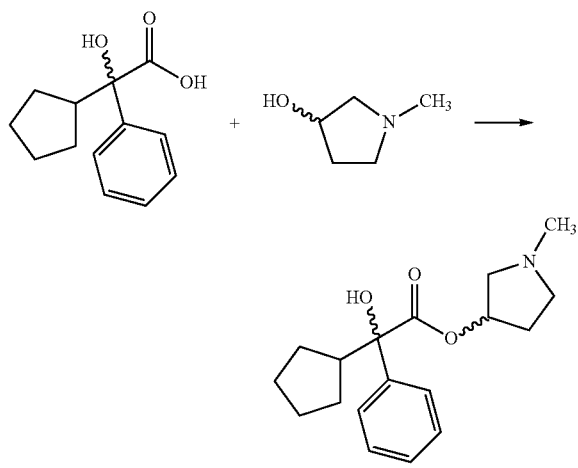

(ii) contacting the glycopyrrolate base with 5-nitroisophthalic acid to form glycopyrrolate base, 5-nitroisophthalate salt:

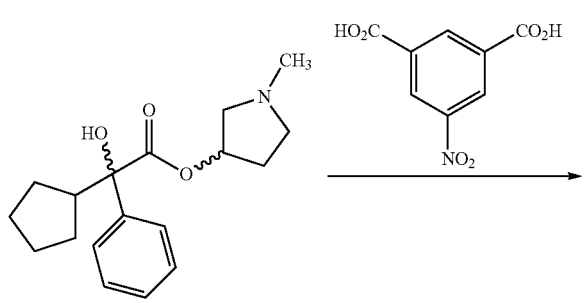

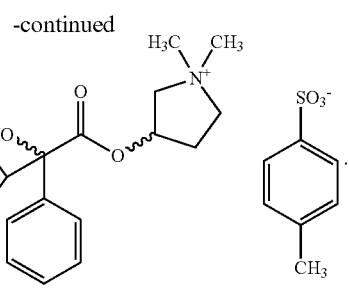

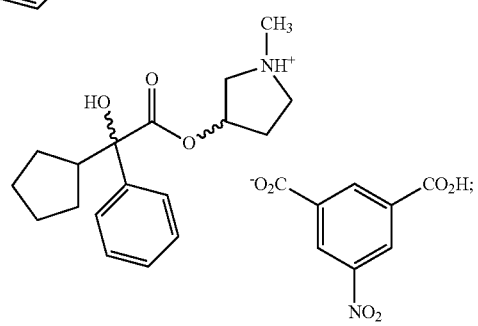

(iii) contacting the glycopyrrolate base, 5-nitroisophthalate salt with an inorganic base to form glycopyrrolate base:

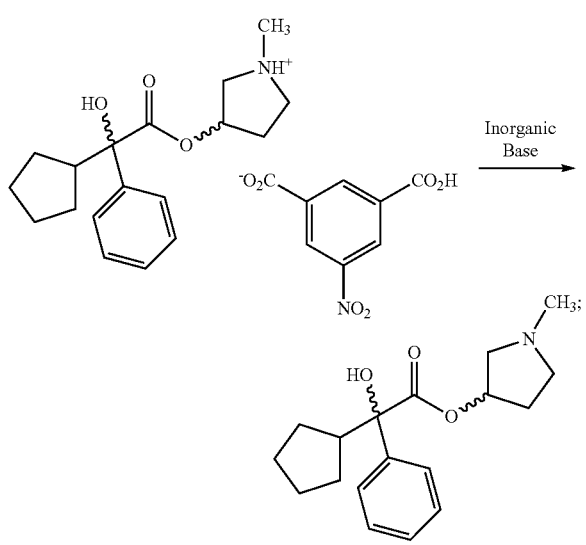

and
(iv) contacting the glycopyrrolate base with methyl tosylate to produce glycopyrronium tosylate:

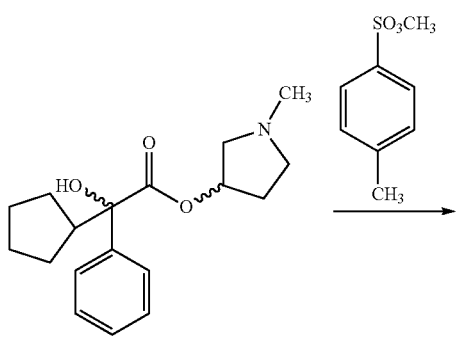

The glycopyrrolate base has two stereocenters, as indicated above. As such, provided herein are glycopyrrolate base compositions comprising a selected mixture of stereoisomers useful in the production of glycopyrronium tosylate. In an embodiment, provided herein is a glycopyrrolate base composition comprising threo-glycopyrrolate base and erythro-glycopyrrolate base, wherein the threo-glycopyrrolate base is at least 95% of the total glycopyrrolate base content of the composition and the erythro-glycopyrrolate base is less than 5% of the total glycopyrrolate base content of the composition.

Also provided herein are glycopyrronium tosylate compositions useful for the treatment of, among other conditions, hyperhidrosis. In an embodiment, provided herein is a glycopyrronium tosylate composition comprising threo-glycopyrronium tosylate and erythro-glycopyrronium tosylate, wherein the threo-glycopyrronium tosylate is at least 95% of the total glycopyrronium tosylate content of the composition and the erythro-glycopyrronium tosylate is less than 5% of the total glycopyrrolate base content of the composition.

DESCRIPTION OF EXEMPLARY EMBODIMENTS

Provided herein are methods of producing glycopyrronium tosylate useful for hyperhidrosis.

Definitions

When referring to the methods and compounds described herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

As used herein, and unless otherwise specified, the term "glycopyrrolate" refers to a cation of a salt containing glycopyrronium. In other words, as used herein, "glycopyrrolate" and "glycopyrronium" are used interchangeably. For example, "glycopyrrolate tosylate" and "glycopyrronium tosylate" refer to the same salt.

As used herein, and unless otherwise specified, the term "glycopyrronium tosylate" refers to a tosylate salt of glycopyrronium. This tosylate salt can be referred to as "3-[(cyclopentylhydroxyphenylacetyl)oxy]-1,1-dimethyl-pyrrolidinium tosylate," or as "3-(2-cyclopentyl-2-hydroxy-2-phenylacetoxy)-1,1-dimethylpyrrolidinium 4-methylbenzenesulfonate." The term "glycopyrronium tosylate" refers to the chemical structure:

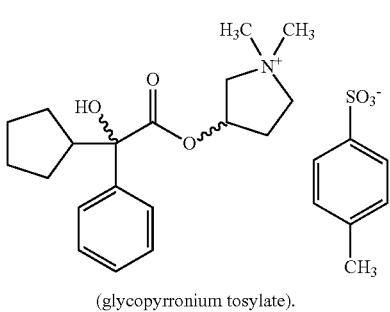

(glycopyrronium tosylate).

Furthermore, the term "glycopyrronium tosylate" as used herein, and unless otherwise specified, includes any one of the four diastereomers listed below as well as any mixture of two, three, or four of the following diastereomers:

(R)-3-((S)-2-cyclopentyl-2-hydroxy-2-phenylacetoxy)-1,1-dimethylpyrrolidinium 4-methylbenzenesulfonate

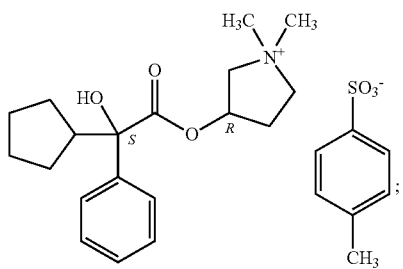

(S)-3-((R)-2-cyclopentyl-2-hydroxy-2-phenylacetoxy)-1,1-dimethylpyrrolidinium 4-methylbenzenesulfonate

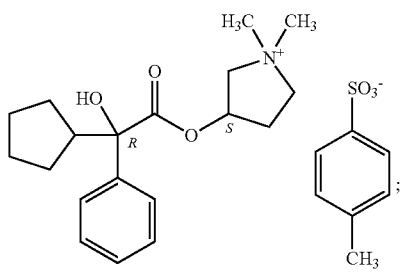

(R)-3-((R)-2-cyclopentyl-2-hydroxy-2-phenylacetoxy)-1,1-dimethylpyrrolidinium 4-methylbenzenesulfonate

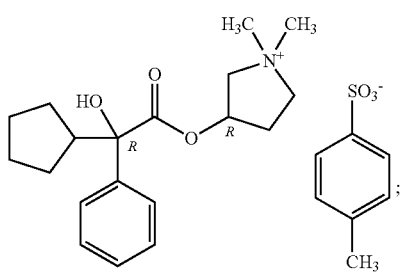

and (S)-3-((S)-2-cyclopentyl-2-hydroxy-2-phenylacetoxy)-1,1-dimethylpyrrolidinium 4-methylbenzenesulfonate

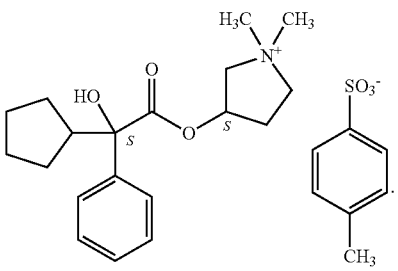

In one embodiment, the "glycopyrronium tosylate" is (R)-3-(S)-2-cyclopentyl-2-hydroxy-2-phenylacetoxy)-1,1-dimethylpyrrolidinium 4-methylbenzenesulfonate. In another embodiment, the "glycopyrronium tosylate" is (S)-3-(R)-2-cyclopentyl-2-hydroxy-2-phenylacetoxy)-1,1-dimethylpyrrolidinium 4-methylbenzenesulfonate. In another embodiment, the "glycopyrronium tosylate" is (R)-3-((R)-2-cyclopentyl-2-hydroxy-2-phenylacetoxy)-1,1-dimethylpyrrolidinium 4-methylbenzenesulfonate. In another embodiment, the "glycopyrronium tosylate" is (S)-3-((S)-2-cyclopentyl-2-hydroxy-2-phenylacetoxy)-1,1-dimethylpyrrolidinium 4-methylbenzenesulfonate. In one embodiment, the "glycopyrronium tosylate" is (R)-3-(S)-2-cyclopentyl-2-hydroxy-2-phenyl acetoxy)-1,1-dimethylpyrrolidinium 4-methylbenzenesulfonate and (S)-3-(R)-2-cyclopentyl-2-hydroxy-2-phenylacetoxy)-1,1-dimethylpyrrolidinium 4-methylbenzenesulfonate. In another embodiment, the "glycopyrronium tosylate" is (R)-3-((R)-2-cyclopentyl-2-hydroxy-2-phenylacetoxy)-1,1-dimethylpyrrolidinium 4-methylbenzenesulfonate and (S)-3-((S)-2-cyclopentyl-2-hydroxy-2-phenylacetoxy)-1,1-dimethylpyrrolidinium 4-methylbenzenesulfonate.

As used herein, the term "threo-glycopyrronium tosylate" refers to a mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate. In certain embodiments "threo-glycopyrronium tosylate" is a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate.

As used herein, the term "erythro-glycopyrronium tosylate" refers to a mixture of (R)-3-((R)-2-cyclopentyl-2-hydroxy-2-phenylacetoxy)-1,1-dimethylpyrrolidinium 4-methylbenzenesulfonate and (S)-3-((S)-2-cyclopentyl-2-hydroxy-2-phenylacetoxy)-1,1-dimethylpyrrolidinium 4-methylbenzenesulfonate. In certain embodiments, "erythro-glycopyrronium tosylate" is a racemic mixture of (R)-3-((R)-2-cyclopentyl-2-hydroxy-2-phenylacetoxy)-1,1-dimethylpyrrolidinium 4-methylbenzenesulfonate and (S)-3-((S)-2-cyclopentyl-2-hydroxy-2-phenylacetoxy)-1,1-dimethylpyrrolidinium 4-methylbenzenesulfonate.

In an embodiment, the "glycopyrronium tosylate" is threo-glycopyrronium tosylate or erythro-glycopyrronium tosylate. In an embodiment, the "glycopyrronium tosylate"

is threo-glycopyrronium tosylate. In an embodiment, the "glycopyrronium tosylate" is erythro-glycopyrronium tosylate.

The terms "substantially free of" and "substantially in the absence of," when used in connection with an article (including, but not limited to, a compound, a salt thereof, a solvate thereof, a solid form thereof, a composition, a mixture of stereoisomers, and the like), refers to the article that includes at least 85% or 90% by weight, in certain embodiments, 95%, 98%, 99%, or 100% by weight, of the designated article. For example, the term "substantially free of" or "substantially in the absence of" with respect to a glycopyrronium tosylate composition can refer to a glycopyrronium tosylate composition that includes at least 85% or 90% by weight, in certain embodiments, 95%, 98%, 99%, or 100% by weight, of the designated diastereomer, or mixture of diastereomers, of glycopyrronium tosylate. In certain embodiments, in the methods, compounds, and compositions provided herein, the compounds or compositions are substantially free of undesignated enantiomers or other compounds or mixtures of enantiomers.

Similarly, the term "isolated" with respect to a glycopyrronium tosylate composition refers to a glycopyrronium tosylate composition that includes at least 85%, 90%, 95%, 98%, or 99% to 100% by weight, of the glycopyrronium tosylate, the remainder comprising other chemical species or enantiomers.

Methods

Provided herein are methods of producing glycopyrronium tosylate. Glycopyrronium tosylate is useful for the treatment of hyperhidrosis.

In an aspect, provided herein are methods of producing glycopyrronium tosylate comprising contacting glycopyrrolate base with methyl tosylate to produce glycopyrronium tosylate:

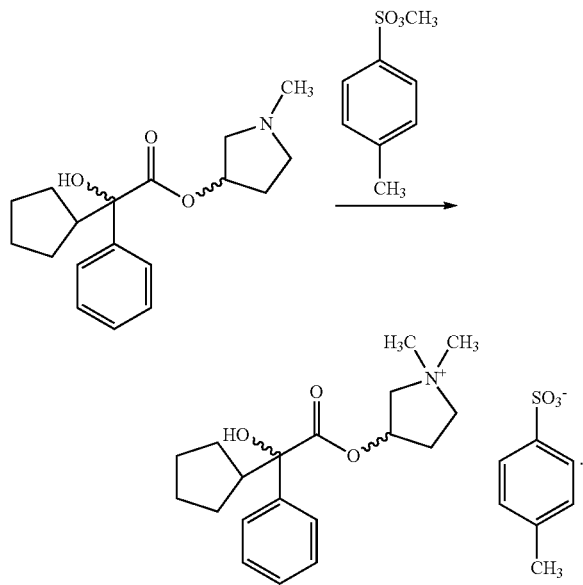

In certain embodiments, the glycopyrrolate base contacted with methyl tosylate is contacted with an organic solvent. In an embodiment, the organic solvent is a water-miscible organic solvent. In an embodiment, the organic solvent is a water-miscible aldehyde, organic acid, ketone, nitrile, diol, alcohol, aminoalcohol, glycol, sulfoxide, ether, cyclic ether, cyclic diether, amine, polyol, or cyclic amine comprising from 1 to 6 carbon atoms. In an embodiment, the organic solvent is acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethyl acetate, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, or triethylene glycol. In an embodiment, the organic solvent is a water-miscible aldehyde, ketone, or ester comprising from 2 to 5 carbon atoms. In an embodiment, the organic solvent is acetone or ethyl acetate. In certain embodiments, the organic solvent is acetone. In certain embodiments, the organic solvent is ethyl acetate.

In an embodiment, the reaction is conducted for at least 2 to 4 hours, optionally at least 2.5 to 3.5 hours, optionally for at least about 3 hours. In an embodiment, the reaction is conducted for about 3 to 21 hours, optionally for about 6 to 18 hours, optionally for about 9 to 15 hours, optionally for about 11 to 13 hours, optionally for about 12 hours. In an embodiment, the reaction is conducted at a temperature selected over the range of 20° C. to 26° C., optionally 22° C. to 24° C., optionally conducted at about 23° C., optionally conducted at about 25° C.

In certain embodiments, the glycopyrronium tosylate produced is substantially in the absence of erythro-glycopyrronium tosylate. In certain embodiments, the glycopyrronium tosylate is isolated threo-glycopyrronium tosylate. In certain embodiments, the glycopyrronium tosylate is a mixture of threo-glycopyrronium tosylate and erythro-glycopyrronium tosylate, and the threo-glycopyrronium tosylate is at least 95% of the total glycopyrronium tosylate mixture and the erythro-glycopyrronium tosylate is less than 5% of the total glycopyrronium tosylate mixture. In certain embodiments, the threo-glycopyrronium tosylate is at least 96% of the total glycopyrronium tosylate mixture and the erythro-glycopyrronium tosylate is less than 4% of the total glycopyrronium tosylate mixture. In certain embodiments, the threo-glycopyrronium tosylate is at least 97% of the total glycopyrronium tosylate mixture and the erythro-glycopyrronium tosylate is less than 3% of the total glycopyrronium tosylate mixture.

In certain embodiments, the glycopyrronium tosylate is purified by one or more crystallizations in an aqueous solvent. In certain embodiments, the aqueous solvent is water. In certain embodiments, the aqueous solvent is water and the glycopyrronium tosylate is purified as isolated threo-glycopyrronium tosylate monohydrate. In certain embodiments, the purified glycopyrronium tosylate is substantially pure. In certain embodiments, the purified glycopyrronium tosylate is a mixture of threo-glycopyrronium tosylate and erythro-glycopyrronium tosylate, and the threo-glycopyrronium tosylate is at least 99% of the total glycopyrronium tosylate in the mixture and the erythro-glycopyrronium tosylate is less than 1% of the total glycopyrronium tosylate in the mixture. In certain embodiments, the threo-glycopyrronium tosylate is at least 99.5% of the total glycopyrronium tosylate in the mixture and the erythro-glycopyrronium tosylate is less than 0.5% of the total glycopyrronium tosylate in the mixture. In certain embodiments, the threo-glycopyrronium tosylate is at least 99.6% of the total glycopyrronium tosylate in the mixture and the erythro-glycopyrronium tosylate is less than 0.4% of the total glycopyrronium tosylate in the mixture.

In certain embodiments, the glycopyrrolate base is produced by contacting a glycopyrrolate base, 5-nitroisophthalate salt with an inorganic base to form the glycopyrrolate base:

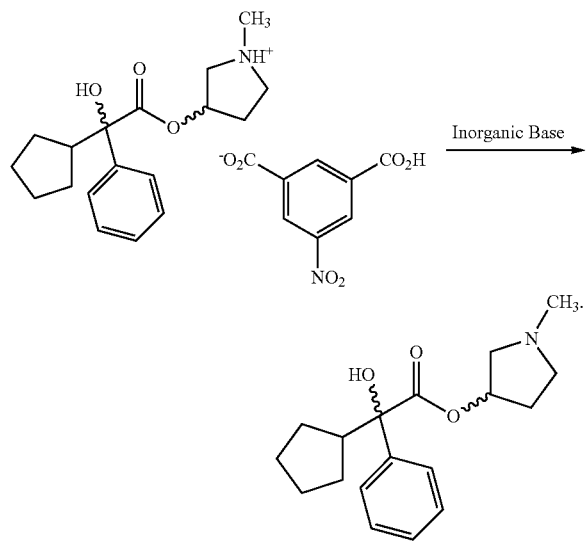

Without wishing to be bound by theory, it is believed threo-glycopyrrolate base, 5-nitroisophthalate salt is less soluble in an organic solvent than erythro-glycopyrrolate base, 5-nitrosiophthalate salt and that this difference in solubility can be used to isolate and purify the threo-glycopyrrolate base. Therefore, in certain embodiments, the glycopyrrolate base, 5-nitroisophthalate salt and inorganic base are contacted with an organic solvent. In certain embodiments, the organic solvent is a water-immiscible organic solvent. In certain embodiments, the water-immiscible organic solvent is benzene, n-butanol, carbon tetrachloride, chloroform, cyclohexane, ethylene chloride, heptane, hexane, pentane, toluene, trichloroethylene, or xylene. In certain embodiments, the organic solvent is toluene. In certain embodiments, the inorganic base is aqueous sodium hydroxide. In certain embodiments, the glycopyrrolate base is produced as a mixture of threo-glycopyrrolate base and erythro-glycopyrrolate base, and the threo-glycopyrrolate base is at least 95% of the total glycopyrrolate base produced and the erythro-glycopyrrolate base is less than 5% of the total glycopyrrolate base produced. In certain embodiments, the threo-glycopyrrolate base is at least 96% of the total glycopyrrolate base produced and the erythro-glycopyrrolate base is less than 4% of the total glycopyrrolate base produced. In certain embodiments, the threo-glycopyrrolate base is at least 97% of the total glycopyrrolate base produced and the erythro-glycopyrrolate base is less than 3% of the total glycopyrrolate base produced.

In an embodiment, the reaction is conducted at a temperature selected over the range of 20° C. to 26° C., optionally 22° C. to 24° C., optionally at about 23° C., optionally at about 25° C. In an embodiment, the reaction mixture is stirred for 5 to 20 minutes, optionally 10 to 15 minutes, optionally 15 minutes. In an embodiment, the pH of the solution in which the reaction is conducted is measured and adjusted to lie within a selected pH range. In an embodiment, the pH range is 11.0 to 13.0, optionally 11.2 to 12.8, optionally 11.5 to 12.5, optionally about 12.0.

In certain embodiments, the glycopyrrolate base, 5-nitroisophthalate salt is produced by contacting a glycopyrrolate base with 5-nitroisophthalic acid to form the glycopyrrolate base, 5-nitroisophthalate salt:

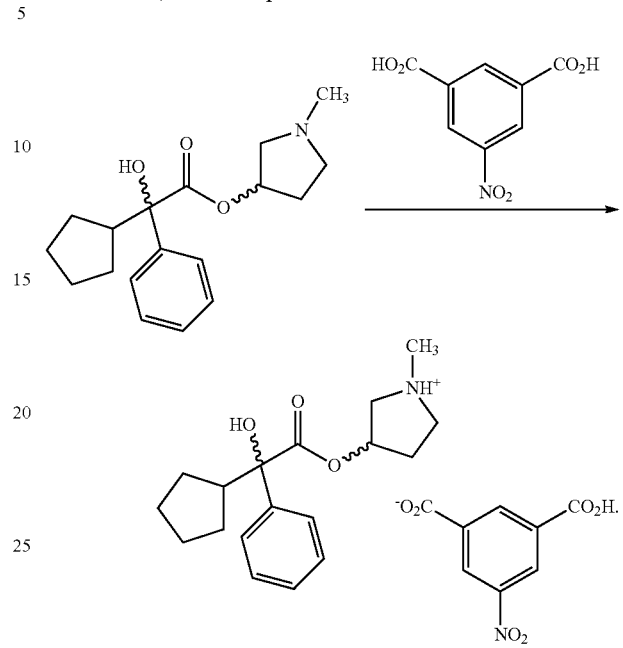

In certain embodiments, the glycopyrrolate base and 5-nitroisophthalic acid are contacted with methanol. In certain embodiments, the glycopyrrolate base, 5-nitroisophthalate salt produced is substantially in the absence of erythro-glycopyrrolate base, 5-nitroisophthalate salt. In an embodiment, the glycopyrrolate base, 5-nitroisophthalate salt is produced as a mixture of threo-glycopyrrolate base, 5-nitroisophthalate salt and erythro-glycopyrrolate base, 5-nitroisophthalate salt, wherein the threo-glycopyrrolate base, 5-nitroisophthalate salt is at least 95% of the total glycopyrrolate base, 5-nitroisophthalate salt produced, and the erythro-glycopyrrolate base, 5-nitroisophthalate salt is less than 5% of the total glycopyrrolate base, 5-nitroisophthalate salt produced. In an embodiment, the threo-glycopyrrolate base, 5-nitroisophthalate salt is at least 96% of the total glycopyrrolate base, 5-nitroisophthalate salt produced and the erythro-glycopyrrolate base, 5-nitroisophthalate salt is less than 4% of the total glycopyrrolate base, 5-nitroisophthalate salt produced. In an embodiment, the threo-glycopyrrolate base, 5-nitroisophthalate salt is at least 97% of the total glycopyrrolate base, 5-nitroisophthalate salt produced and the erythro-glycopyrrolate base, 5-nitroisophthalate salt is less than 3% of the total glycopyrrolate base, 5-nitroisophthalate salt produced.

In an embodiment, the reaction is conducted for 3 to 5 hours, optionally for 3.5 to 4.5 hours, optionally for about 4 hours. In an embodiment, the reaction is conducted at a temperature selected over the range of 20° C. to 26° C., optionally 22° C. to 24° C., optionally at about 23° C., optionally at about 25° C.

In certain embodiments, the glycopyrrolate base is produced by contacting cyclopentylmandelic acid with 1-methylpyrrolidin-3-ol to form the glycopyrrolate base:

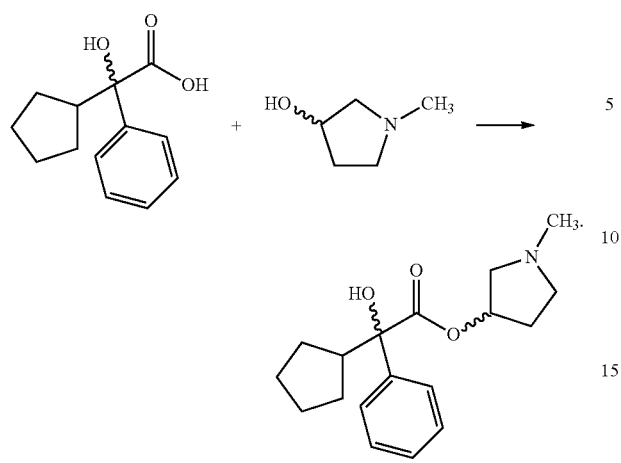

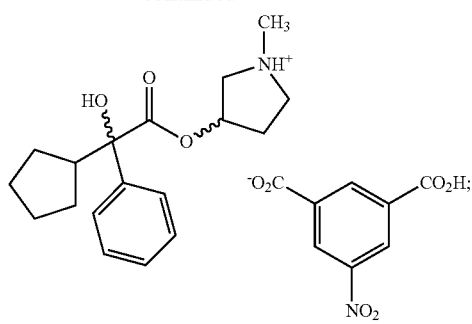

(iii) contacting the glycopyrrolate base, 5-nitroisophthalate salt with an inorganic base to form glycopyrrolate base:

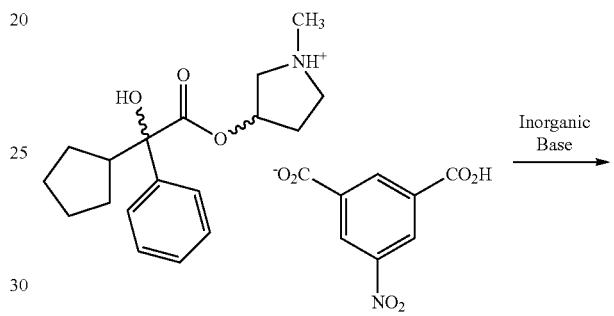

In an embodiment, the glycopyrrolate base is produced as a mixture of threo-glycopyrrolate base and erythro-glycopyrrolate base. In an embodiment, the glycopyrrolate base is produced as a racemic mixture of threo-glycopyrrolate base and erythro-glycopyrrolate base.

In an aspect, provided herein is a method of producing glycopyrronium tosylate comprising:

(i) contacting cyclopentylmandelic acid with 1-methyl-pyrrolidin-3-ol to form glycopyrrolate base:

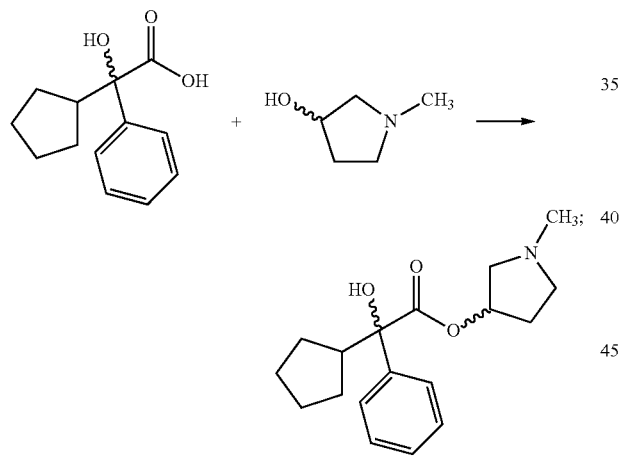

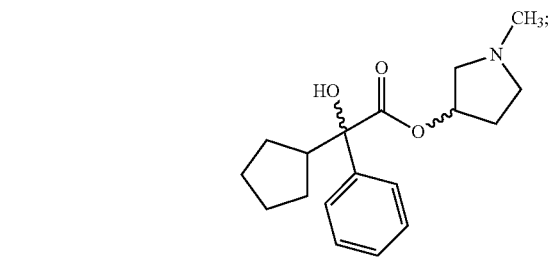

and (iv) contacting the glycopyrrolate base with methyl tosylate to produce glycopyrronium tosylate:

(ii) contacting the glycopyrrolate base with 5-nitroisophthalic acid to form glycopyrrolate base, 5-nitroisophthalate salt:

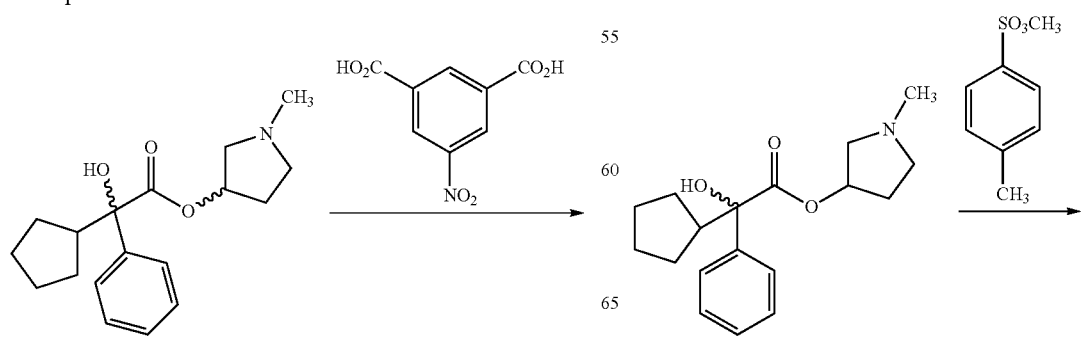

-continued

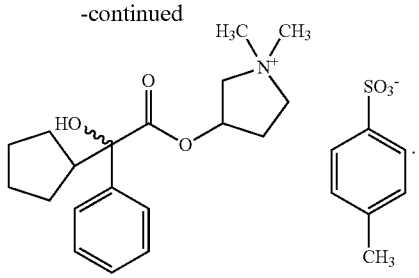

In an embodiment, the glycopyrrolate base formed in step (i) is a mixture of four diastereomers (i.e., comprises both the threo and erythro pairs of diastereomers). In an embodiment, the glycopyrrolate base formed in step (i) is a racemic mixture of four diastereomers (i.e., comprises equal amounts of both the threo and erythro pairs of diastereomers).

In and embodiment, the glycopyrrolate base, 5-nitroisophthalate salt produced in step (ii) is substantially in the absence of erythro-glycopyrrolate base, 5-nitroisophthalate salt. In an embodiment, the glycopyrrolate base, 5-nitroisophthalate salt formed in step (ii) is produced as a mixture of threo-glycopyrrolate base, 5-nitroisophthalate salt and erythro-glycopyrrolate base, 5-nitroisophthalate salt, wherein the threo-glycopyrrolate base, 5-nitroisophthalate salt is at least 95% of the total glycopyrrolate base, 5-nitroisophthalate salt produced, and the erythro-glycopyrrolate base, 5-nitroisophthalate salt is less than 5% of the total glycopyrrolate base, 5-nitroisophthalate salt produced. In an embodiment, the threo-glycopyrrolate base, 5-nitroisophthalate salt is at least 96% of the total glycopyrrolate base, 5-nitroisophthalate salt produced and the erythro-glycopyrrolate base, 5-nitroisophthalate salt is less than 4% of the total glycopyrrolate base, 5-nitroisophthalate salt produced. In an embodiment, the threo-glycopyrrolate base, 5-nitroisophthalate salt is at least 97% of the total glycopyrrolate base, 5-nitroisophthalate salt produced and the erythro-glycopyrrolate base, 5-nitroisophthalate salt is less than 3% of the total glycopyrrolate base, 5-nitroisophthalate salt produced.

Without wishing to be bound by theory, it is believed threo-glycopyrrolate base, 5-nitroisophthalate salt is less soluble in an organic solvent than erythro-glycopyrrolate base, 5-nitrosiophthalate salt and that this difference in solubility can be used to isolate and purify the threo-glycopyrrolate base. Therefore, in an embodiment, in step (iii) the glycopyrrolate base, 5-nitroisophthalate salt and inorganic base are contacted with an organic solvent. In certain embodiments, the organic solvent is a water-immiscible organic solvent. In certain embodiments, the water-immiscible organic solvent is benzene, n-butanol, carbon tetrachloride, chloroform, cyclohexane, ethylene chloride, heptane, hexane, pentane, toluene, trichloroethylene, or xylene. In an embodiment, the organic solvent is toluene.

In an embodiment, in step (iii) the inorganic base is aqueous sodium hydroxide. In an embodiment, in step (iii) the inorganic base is aqueous sodium hydroxide and the glycopyrrolate base, 5-nitroisophthalate salt and inorganic base are contacted with an organic solvent. In certain embodiments, the organic solvent is a water-immiscible organic solvent. In certain embodiments, the water-immiscible organic solvent is benzene, n-butanol, carbon tetrachloride, chloroform, cyclohexane, ethylene chloride, heptane, hexane, pentane, toluene, trichloroethylene, or xylene. In an embodiment, the organic solvent is toluene.

In an embodiment, the glycopyrrolate base produced in step (iii) is produced as a mixture of threo-glycopyrrolate base and erythro-glycopyrrolate base, the threo-glycopyrrolate base is at least 95% of the total glycopyrrolate base produced, and the erythro-glycopyrrolate base is less than 5% of the total glycopyrrolate base produced. In an embodiment, the threo-glycopyrrolate base is at least 96% of the total glycopyrrolate base produced and the erythro-glycopyrrolate base is less than 4% of the total glycopyrrolate base produced. In an embodiment, the threo-glycopyrrolate base is at least 97% of the total glycopyrrolate base produced and the erythro-glycopyrrolate base is less than 3% of the total glycopyrrolate base produced.

In an embodiment, the glycopyrronium tosylate produced in step (iv) is produced as a mixture of threo-glycopyrronium tosylate and erythro-glycopyrronium tosylate, wherein the threo-glycopyrronium tosylate is at least 95% of the total glycopyrronium tosylate mixture, and the erythro-glycopyrronium tosylate is less than 5% of the total glycopyrronium tosylate mixture. In an embodiment, the threo-glycopyrronium tosylate is at least 96% of the total glycopyrronium tosylate mixture and the erythro-glycopyrronium tosylate is less than 4% of the total glycopyrronium tosylate mixture. In an embodiment, the threo-glycopyrronium tosylate is at least 97% of the total glycopyrronium tosylate mixture and the erythro-glycopyrronium tosylate is less than 3% of the total glycopyrronium tosylate mixture.

In an embodiment, the glycopyrronium tosylate is purified by one or more (re)crystallizations in an aqueous solvent. In an embodiment, the aqueous solvent is water. In an embodiment, the glycopyrronium tosylate following (re)crystallization in water is in the form of glycopyrronium tosylate monohydrate. In an embodiment, the amount of water in the glycopyrronium tosylate monohydrate is less than about 5% weight water to weight glycopyrronium tosylate, optionally less than about 4% weight water to weight glycopyrronium tosylate, optionally about 3.5% weight water to weight glycopyrronium tosylate. In an embodiment, the purified glycopyrronium tosylate is a mixture of threo-glycopyrronium tosylate and erythro-glycopyrronium tosylate, wherein the threo-glycopyrronium tosylate is at least 99% of the total glycopyrronium tosylate in the mixture, and the erythro-glycopyrronium tosylate is less than 1% of the total glycopyrronium tosylate in the mixture. In an embodiment, the threo-glycopyrronium tosylate is at least 99.5% of the total glycopyrronium tosylate in the mixture and the erythro-glycopyrronium tosylate is less than 0.5% of the total glycopyrronium tosylate in the mixture. In an embodiment, the threo-glycopyrronium tosylate is at least 99.6% of the total glycopyrronium tosylate in the mixture and the erythro-glycopyrronium tosylate is less than 0.4% of the total glycopyrronium tosylate in the mixture.

In an embodiment, in step (iv) the glycopyrrolate base and methyl tosylate are contacted with an organic solvent. In certain embodiments, the glycopyrrolate base contacted with methyl tosylate is contacted with an organic solvent. In an embodiment, the organic solvent is a water-miscible organic solvent. In an embodiment, the organic solvent is a water-miscible aldehyde, organic acid, ketone, nitrile, diol, alcohol, aminoalcohol, glycol, sulfoxide, ether, cyclic ether, cyclic diether, amine, polyol, or cyclic amine comprising from 1 to 6 carbon atoms. In an embodiment, the organic solvent is acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethyl acetate, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, or triethylene glycol. In an embodiment, the organic solvent is a water-miscible aldehyde, ketone, or ester comprising from 2 to 5 carbon atoms. In an embodiment, the organic solvent is acetone or ethyl acetate. In certain embodiments, the organic solvent is acetone. In certain embodiments, the organic solvent is ethyl acetate.

In an embodiment, the reaction in step (ii) is conducted for 3 to 5 hours, optionally for 3.5 to 4.5 hours, optionally for about 4 hours. In an embodiment, the reaction in step (ii) is conducted at a temperature selected over the range of 20° C. to 26° C., optionally 22° C. to 24° C., optionally at about 23° C., optionally at about 25° C.

In an embodiment, the reaction in step (iii) is conducted at a temperature selected over the range of 20° C. to 26° C., optionally 22° C. to 24° C., optionally at about 23° C., optionally at about 25° C. In an embodiment, the reaction mixture in step (iii) is stirred for 5 to 20 minutes, optionally 10 to 15 minutes, optionally 15 minutes. In an embodiment, the pH of the solution in which the reaction in step (iii) is conducted is measured and adjusted to lie within a selected pH range. In an embodiment, the pH range is 11.0 to 13.0, optionally 11.2 to 12.8, optionally 11.5 to 12.5, optionally about 12.0.

In an embodiment, the reaction in step (iv) is conducted for at least 2 to 4 hours, optionally at least 2.5 to 3.5 hours, optionally for at least about 3 hours. In an embodiment, the reaction in step (iv) is conducted for about 3 to 21 hours, optionally for about 6 to 18 hours, optionally for about 9 to 15 hours, optionally for about 11 to 13 hours, optionally for about 12 hours. In an embodiment, the reaction in step (iv) is conducted at a temperature selected over the range of 20° C. to 26° C., optionally 22° C. to 24° C., optionally conducted at about 23° C., optionally conducted at about 25° C.

Compositions

Provided herein are glycopyrronium tosylate compositions and compositions useful in the preparation of glycopyrronium tosylate.

In an aspect, provided herein is a glycopyrrolate base composition comprising threo-glycopyrrolate base and erythro-glycopyrrolate base, wherein the composition is produced by:

(i) contacting cyclopentylmandelic acid with 1-methylpyrrolidin-3-ol to form glycopyrrolate base:

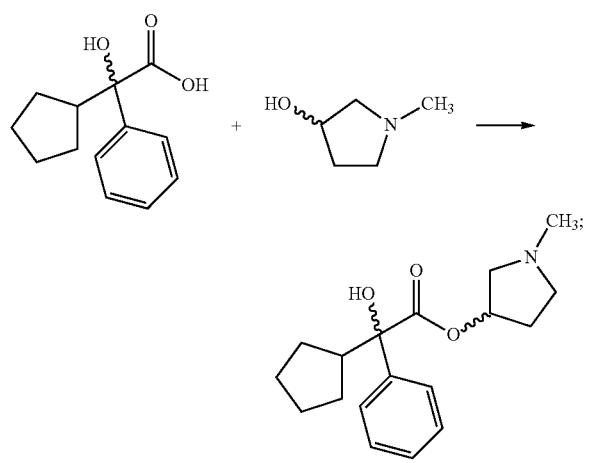

(ii) contacting the glycopyrrolate base with 5-nitroisophthalic acid to form glycopyrrolate base, 5-nitroisophthalate salt:

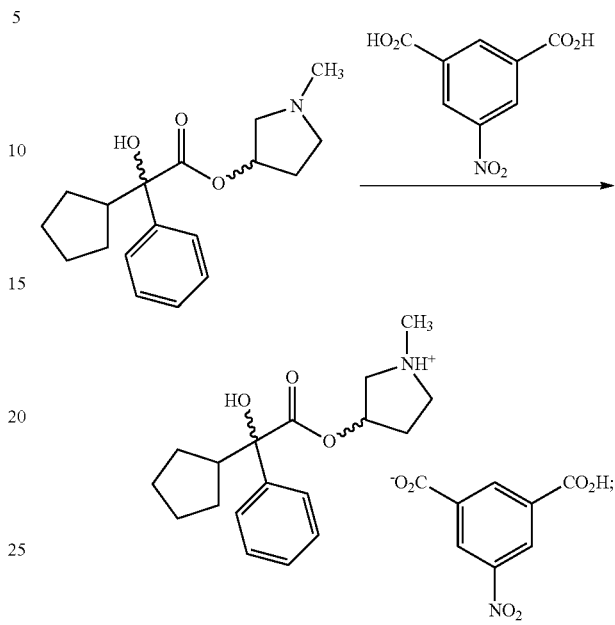

(iii) contacting the glycopyrrolate base, 5-nitroisophthalate salt with an inorganic base to form glycopyrrolate base: and

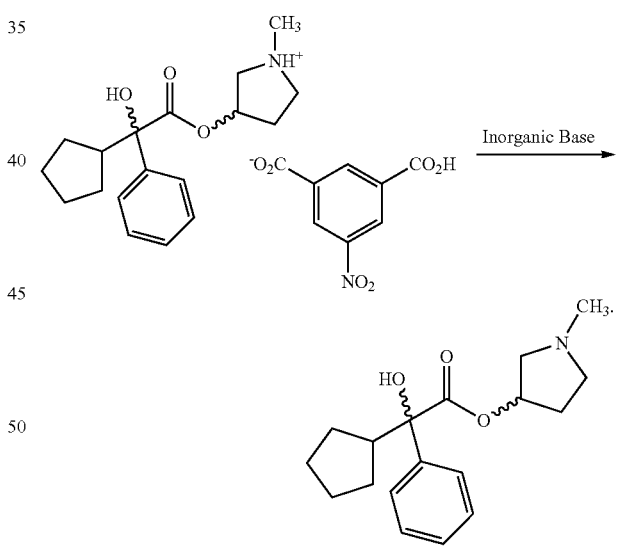

In an embodiment, the glycopyrrolate base formed in step (i) is a mixture of four diastereomers (i.e., comprises both the threo and erythro pairs of diastereomers). In an embodiment, the glycopyrrolate base formed in step (i) is a racemic mixture of four diastereomers (i.e., comprises equal amounts of both the threo and erythro pairs of diastereomers).

In an embodiment, the glycopyrrolate base, 5-nitroisophthalate salt formed in step (ii) is produced as a mixture of threo-glycopyrrolate base, 5-nitroisophthalate salt and erythro-glycopyrrolate base, 5-nitroisophthalate salt, wherein the threo-glycopyrrolate base, 5-nitroisophthalate salt is at least 95% of the total glycopyrrolate base, 5-nitroisophthalate salt produced, and the erythro-glycopyrrolate base, 5-nitroisophthalate salt is less than 5% of the total glycopyrrolate base, 5-nitroisophthalate salt produced. In an embodiment, the threo-glycopyrrolate base, 5-nitroisophthalate salt is at least 96% of the total glycopyrrolate base, 5-nitroisophthalate salt produced and the erythro-glycopyrrolate base, 5-nitroisophthalate salt is less than 4% of the total glycopyrrolate base, 5-nitroisophthalate salt produced. In an embodiment, the threo-glycopyrrolate base, 5-nitroisophthalate salt is at least 97% of the total glycopyrrolate base, 5-nitroisophthalate salt produced and the erythro-glycopyrrolate base, 5-nitroisophthalate salt is less than 3% of the total glycopyrrolate base, 5-nitroisophthalate salt produced.

Without wishing to be bound by theory, it is believed threo-glycopyrrolate base, 5-nitroisophthalate salt is less soluble in an organic solvent than erythro-glycopyrrolate base, 5-nitroisophthalate salt and that this difference in solubility can be used to isolate and purify the threo-glycopyrrolate base. Therefore, in an embodiment, in step (iii) the glycopyrrolate base, 5-nitroisophthalate salt and inorganic base are contacted with an organic solvent. In certain embodiments, the organic solvent is a water-immiscible organic solvent. In certain embodiments, the water-immiscible organic solvent is benzene, n-butanol, carbon tetrachloride, chloroform, cyclohexane, ethylene chloride, heptane, hexane, pentane, toluene, trichloroethylene, or xylene. In an embodiment, the organic solvent is toluene. In an embodiment, in step (iii) the inorganic base is aqueous sodium hydroxide. In an embodiment, the threo-glycopyrrolate base is at least 95% of the total glycopyrrolate base content of the composition and the erythro-glycopyrrolate base is less than 5% of the total glycopyrrolate base content of the composition. In an embodiment, the threo-glycopyrrolate base is at least 96% of the total glycopyrrolate base content of the composition and the erythro-glycopyrrolate base is less than 4% of the total glycopyrrolate base content of the composition. In an embodiment, the threo-glycopyrrolate base is at least 97% of the total glycopyrrolate base content of the composition and the erythro-glycopyrrolate base is less than 3% of the total glycopyrrolate base content of the composition.

In an aspect, provided herein is a glycopyrronium tosylate composition comprising threo-glycopyrronium tosylate and erythro-glycopyrronium tosylate, wherein the threo-glycopyrronium tosylate is at least 95% of the total glycopyrronium tosylate content of the composition and the erythro-glycopyrronium tosylate is less than 5% of the total glycopyrrolate base content of the composition. In an embodiment, the threo-glycopyrronium tosylate is at least 96% of the total glycopyrronium tosylate content of the composition and the erythro-glycopyrronium tosylate is less than 4% of the total glycopyrronium tosylate content of the composition. In an embodiment, the threo-glycopyrronium tosylate is at least 97% of the total glycopyrronium tosylate content of the composition and the erythro-glycopyrronium tosylate is less than 3% of the total glycopyrronium tosylate content of the composition. In an embodiment, the threo-glycopyrronium tosylate is at least 99% of the total glycopyrronium tosylate content of the composition and the erythro-glycopyrronium tosylate is less than 1% of the total glycopyrronium tosylate content of the composition. In an embodiment, the threo-glycopyrronium tosylate is at least 99.5% of the total glycopyrronium tosylate content of the composition and the erythro-glycopyrronium tosylate is less than 0.5% of the total glycopyrronium tosylate content of the composition. In an embodiment, the threo-glycopyrronium tosylate is at least 99.6% of the total glycopyrronium tosylate content of the composition and the erythro-glycopyrronium tosylate is less than 0.4% of the total glycopyrronium tosylate content of the composition.

In an aspect, provided herein is a glycopyrronium tosylate composition comprising threo-glycopyrronium tosylate and erythro-glycopyrronium tosylate, wherein:

the threo-glycopyrronium tosylate is at least 95% of the total glycopyrronium tosylate content of the composition;

the erythro-glycopyrronium tosylate is less than 5% of the total glycopyrronium base content of the composition; and the composition is produced by:

(i) contacting cyclopentylmandelic acid with 1-methyl-pyrrolidin-3-ol to form glycopyrrolate base:

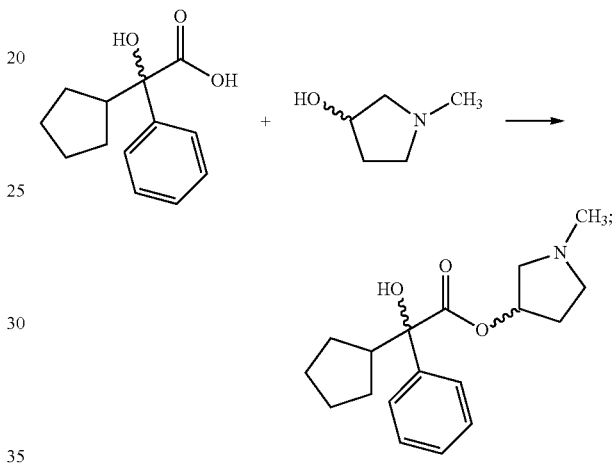

(ii) contacting the glycopyrrolate base with 5-nitroisophthalic acid to form glycopyrrolate base, 5-nitroisophthalate salt:

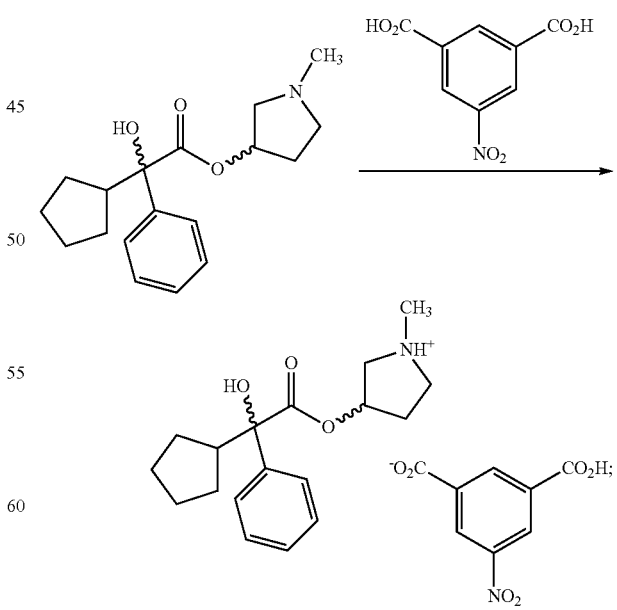

(iii) contacting the glycopyrrolate base, 5-nitroisophthalate salt with an inorganic base to form glycopyrrolate base:

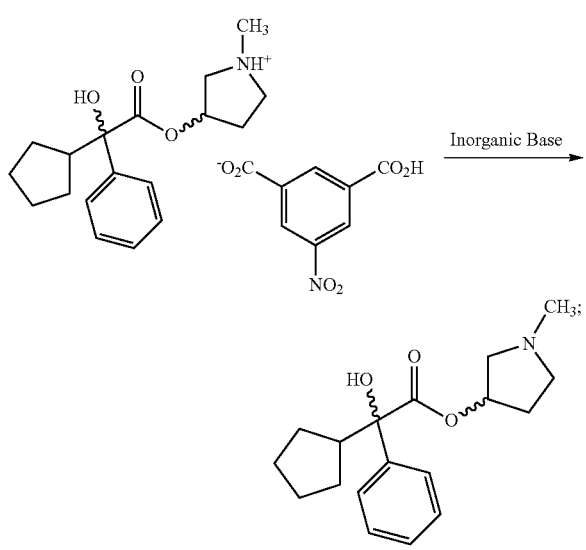

and (iv) contacting the glycopyrrolate base with methyl tosylate to produce glycopyrronium tosylate:

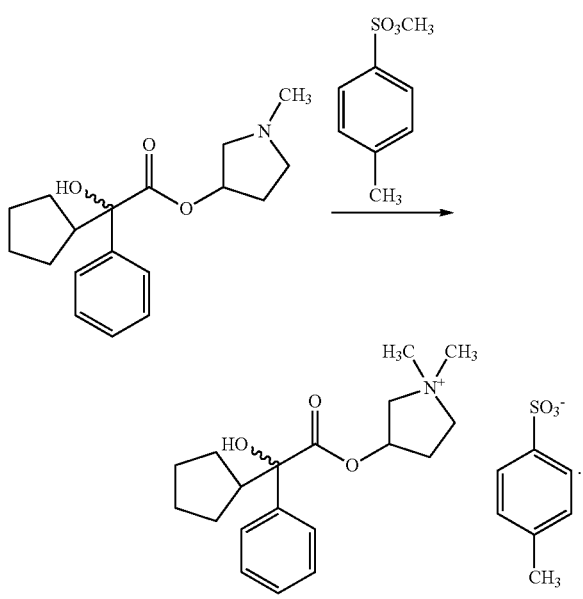

Without wishing to be bound by theory, it is believed threo-glycopyrrolate base, 5-nitroisophthalate salt is less soluble in an organic solvent than erythro-glycopyrrolate base, 5-nitroisophthalate salt and that this difference in solubility can be used to isolate and purify the threo-glycopyrrolate base. Therefore, in an embodiment, in step (iii) the glycopyrrolate base, 5-nitroisophthalate salt and inorganic base are contacted with an organic solvent. In certain embodiments, the organic solvent is a water-immiscible organic solvent. In certain embodiments, the water-immiscible organic solvent is benzene, n-butanol, carbon tetrachloride, chloroform, cyclohexane, ethylene chloride, heptane, hexane, pentane, toluene, trichloroethylene, or xylene. In an embodiment, the organic solvent is toluene. In an embodiment, in step (iii) the inorganic base is aqueous sodium hydroxide. In an embodiment, the glycopyrrolate base produced in step (iii) is produced as a mixture of threo-glycopyrrolate base and erythro-glycopyrrolate base, wherein the threo-glycopyrrolate base is at least 95% of the total glycopyrrolate base produced, and the erythro-glycopyrrolate base is less than 5% of the total glycopyrrolate base produced. In an embodiment, the threo-glycopyrrolate base is at least 96% of the total glycopyrrolate base produced and the erythro-glycopyrrolate base is less than 4% of the total glycopyrrolate base produced. In an embodiment, the threo-glycopyrrolate base is at least 97% of the total glycopyrrolate base produced and the erythro-glycopyrrolate base is less than 3% of the total glycopyrrolate base produced.

In an embodiment, the glycopyrrolate base formed in step (i) is a mixture of four diastereomers (i.e., comprises both the threo and erythro pairs of diastereomers). In an embodiment, the glycopyrrolate base formed in step (i) is a racemic mixture of four diastereomers (i.e., comprises equal amounts of both the threo and erythro pairs of diastereomers).

In an embodiment, the glycopyrrolate base, 5-nitroisophthalate salt formed in step (ii) is produced as a mixture of threo-glycopyrrolate base, 5-nitroisophthalate salt and erythro-glycopyrrolate base, 5-nitroisophthalate salt, wherein the threo-glycopyrrolate base, 5-nitroisophthalate salt is at least 95% of the total glycopyrrolate base, 5-nitroisophthalate salt produced, and the erythro-glycopyrrolate base, 5-nitroisophthalate salt is less than 5% of the total glycopyrrolate base, 5-nitroisophthalate salt produced. In an embodiment, the threo-glycopyrrolate base, 5-nitroisophthalate salt is at least 96% of the total glycopyrrolate base, 5-nitroisophthalate salt produced and the erythro-glycopyrrolate base, 5-nitroisophthalate salt is less than 4% of the total glycopyrrolate base, 5-nitroisophthalate salt produced. In an embodiment, the threo-glycopyrrolate base, 5-nitroisophthalate salt is at least 97% of the total glycopyrrolate base, 5-nitroisophthalate salt produced and the erythro-glycopyrrolate base, 5-nitroisophthalate salt is less than 3% of the total glycopyrrolate base, 5-nitroisophthalate salt produced.

In an embodiment, the glycopyrronium tosylate produced in step (iv) is produced as a mixture of threo-glycopyrronium tosylate and erythro-glycopyrronium tosylate, wherein the threo-glycopyrronium tosylate is at least 95% of the total glycopyrronium tosylate mixture, and the erythro-glycopyrronium tosylate is less than 5% of the total glycopyrronium tosylate mixture. In an embodiment, the threo-glycopyrronium tosylate is at least 96% of the total glycopyrronium tosylate mixture and the erythro-glycopyrronium tosylate is less than 4% of the total glycopyrronium tosylate mixture. In an embodiment, the threo-glycopyrronium tosylate is at least 97% of the total glycopyrronium tosylate mixture and the erythro-glycopyrronium tosylate is less than 3% of the total glycopyrronium tosylate mixture.

In an embodiment, the glycopyrronium tosylate is purified by one or more (re)crystallizations in an aqueous solvent. In an embodiment, the aqueous solvent is water. In an embodiment, the glycopyrronium tosylate following (re)crystallization in water is in the form of glycopyrronium tosylate monohydrate. In an embodiment, the amount of water in the glycopyrronium tosylate monohydrate is less than about 5% weight water to weight glycopyrronium tosylate, optionally less than about 4% weight water to weight glycopyrronium tosylate, optionally about 3.5% weight water to weight glycopyrronium tosylate. In an embodiment, the purified glycopyrronium tosylate is a mixture of threo-glycopyrronium tosylate and erythro-glycopyrronium tosylate, wherein the threo-glycopyrronium tosylate is at least 99% of the total glycopyrronium tosylate in the mixture, and the erythro-glycopyrronium tosylate is less than 1% of the total glycopyrronium tosylate in the mixture. In an embodiment, the threo-glycopyrronium tosylate is at least 99.5% of the total glycopyrronium tosylate in the mixture and the erythro-glycopyrronium tosylate is less than 0.5% of the total glycopyrronium tosylate in the mixture. In an embodiment, the threo-glycopyrronium tosylate is at least 99.6% of the total glycopyrronium tosylate in the mixture and the erythro-glycopyrronium tosylate is less than 0.4% of the total glycopyrronium tosylate in the mixture.

In an embodiment, in step (iv) the glycopyrrolate base and methyl tosylate are contacted with an organic solvent. In certain embodiments, the glycopyrrolate base contacted with methyl tosylate is contacted with an organic solvent. In an embodiment, the organic solvent is a water-miscible organic solvent. In an embodiment, the organic solvent is a water-miscible aldehyde, organic acid, ketone, nitrile, diol, alcohol, aminoalcohol, glycol, sulfoxide, ether, cyclic ether, cyclic diether, amine, polyol, or cyclic amine comprising from 1 to 6 carbon atoms. In an embodiment, the organic solvent is acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethyl acetate, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, or triethylene glycol. In an embodiment, the organic solvent is a water-miscible aldehyde, ketone, or ester comprising from 2 to 5 carbon atoms. In an embodiment, the organic solvent is acetone or ethyl acetate. In certain embodiments, the organic solvent is acetone. In certain embodiments, the organic solvent is ethyl acetate.

In certain embodiments, the glycopyrronium tosylate composition is substantially free of erythro-glycopyrronium tosylate. In an embodiment, at least 90% of the glycopyrronium tosylate in the composition is threo-glycopyrronium tosylate. In an embodiment, at least 91% of the glycopyrronium tosylate in the composition is threo-glycopyrronium tosylate. In an embodiment, at least 92% of the glycopyrronium tosylate in the composition is threo-glycopyrronium tosylate. In an embodiment, at least 93% of the glycopyrronium tosylate in the composition is threo-glycopyrronium tosylate. In an embodiment, at least 94% of the glycopyrronium tosylate in the composition is threo-glycopyrronium tosylate. In an embodiment, at least 95% of the glycopyrronium tosylate in the composition is threo-glycopyrronium tosylate. In an embodiment, at least 96% of the glycopyrronium tosylate in the composition is threo-glycopyrronium tosylate. In an embodiment, at least 97% of the glycopyrronium tosylate in the composition is threo-glycopyrronium tosylate. In an embodiment, at least 98% of the glycopyrronium tosylate in the composition is threo-glycopyrronium tosylate. In an embodiment, at least 99% of the glycopyrronium tosylate in the composition is threo-glycopyrronium tosylate.

Methods of Treatment

Provided herein are methods of treating a disorder comprising administering an effective treatment amount of a glycopyrronium tosylate composition described herein. In an embodiment, provided herein is a method of treating hyperhidrosis comprising administering an effective treatment amount of a glycopyrronium tosylate composition described herein. In an embodiment, provided herein is a method of treating hyperhidrosis comprising administering an effective treatment amount of a glycopyrronium tosylate composition described herein, wherein the glycopyrronium tosylate composition is administered topically. In an embodiment, provided herein is a method of treating hyperhidrosis comprising administering an effective treatment amount of a glycopyrronium tosylate composition described herein, wherein the glycopyrronium tosylate composition is administered topically with a wipe.

Pharmaceutical Compositions and Methods of Administration

The glycopyrronium tosylate compositions can be formulated into pharmaceutical compositions using methods available in the art and those disclosed herein. Any of the glycopyrronium tosylate compositions disclosed herein can be provided in the appropriate pharmaceutical composition and be administered by a suitable route of administration.

The methods provided herein encompass administering pharmaceutical compositions containing at least one glycopyrronium tosylate composition as described herein, either used alone or in the form of a combination with one or more compatible and pharmaceutically acceptable carriers, such as diluents or adjuvants, or with another therapeutic agent.

In certain embodiments, the second agent can be formulated or packaged with the glycopyrronium tosylate composition provided herein. Of course, the second agent will only be formulated with the glycopyrronium tosylate composition provided herein when, according to the judgment of those of skill in the art, such co-formulation should not interfere with the activity of either agent or the method of administration. In certain embodiments, the glycopyrronium tosylate composition provided herein and the second agent are formulated separately. They can be packaged together, or packaged separately, for the convenience of the practitioner of skill in the art.

In clinical practice the active agents provided herein may be administered by any conventional route. In certain embodiments, the glycopyrronium tosylate composition provided herein is administered topically. In certain embodiments, the glycopyrronium tosylate composition provided herein is administered topically with a wipe.

In certain embodiments, a composition provided herein is a pharmaceutical composition. Pharmaceutical compositions provided herein comprise a prophylactically or therapeutically effective amount of one or more prophylactic or therapeutic agents (e.g., a glycopyrronium tosylate composition provided herein, or other prophylactic or therapeutic agent), and typically one or more pharmaceutically acceptable carriers or excipients. In a specific embodiment and in this context, the term "pharmaceutically acceptable" means approved by a regulatory agency of a government, or listed in the U.S. Pharmacopeia or other generally recognized pharmacopeia for use in animals, and more particularly in humans.

The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Typical dosage forms comprising a glycopyrronium tosylate composition provided herein, or a pharmaceutically acceptable solvate or hydrate thereof, lie within the range of from about 50 mg to about 150 mg of active compound per day, given as a single once-a-day dose in the morning or as divided doses throughout the day. Particular dosage forms can have about 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 110, 115, 120, 125, 130, 135, 140, 145, or 150 mg of the active compound.

Topical Dosage Forms

Also provided are topical dosage forms. Topical dosage forms include, but are not limited to, sprays, aerosols, creams, lotions, ointments, gels, solutions, emulsions, suspensions, or other forms known to one of skill in the art. See, e.g., Remington's Pharmaceutical Sciences, $16^{th}$, $18^{th}$, $20^{th}$, and $22^{nd}$ eds., Mack Publishing, Easton Pa. (1980, 1990, 2000 & 2012); and Introduction to Pharmaceutical Dosage Forms, 4th ed., Lea & Febiger, Philadelphia (1985).

Suitable excipients (e.g., carriers and diluents) and other materials that can be used to provide topical dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, $18^{th}$, $20^{th}$, and $22^{nd}$ eds., Mack Publishing, Easton Pa. (1980, 1990, 2000 & 2012).

In an embodiment, provided herein is a topical dosage form comprising about 50-150 mg of active compound in an alcohol:water solution and with a pH buffering agent. In an embodiment, the active compound is about 0.25-6% of the topical dosage form. In an embodiment, the topical dosage form comprises about 70-105 mg of active compound. In an embodiment, the topical dosage form comprises about 70 mg of active compound. In an embodiment, the topical dosage form comprises about 105 mg of active compound. In an embodiment, the alcohol:water ratio of the topical dosage form is selected over the range of 50:50 to 70:30, preferably over the range of 53:47 to 58:42. In an embodiment, the buffering agent is about 0.2 to 0.5% of the topical dosage form. In an embodiment, the buffering agent of the topical dosage form is citric acid/sodium citrate. In an embodiment, the pH of the topical dosage form is selected over the range of 4.0 to 5.0. In an embodiment, the pH of the topical dosage form is about 4.5.

In an embodiment, the topical dosage form is provided in a wipe for topical administration. In an embodiment, the topical dosage form is provided in a wipe soaked with the topical dosage form. In an embodiment, the topical dosage form is provided in a wipe soaked with the topical dosage form provided in a package comprising several wipes per package.

Dosage and Unit Dosage Forms

In human therapeutics, the doctor will determine the posology which he considers most appropriate according to a preventive or curative treatment and according to the age, weight, stage of the disorder and other factors specific to the subject to be treated. Alternatively, the posology will be provided on or in packaging providing in an over-the-counter kit comprising a dosage form. In certain embodiments, doses are from about 50 mg to about 150 mg active compound per day for an adult. Particular dosage forms can have about 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 110, 115, 120, 125, 130, 135, 140, 145, or 150 mg of the active compound.

In further aspects, provided are methods of treating or preventing a disorder of a subject by administering, to a subject in need thereof, an effective amount of a glycopyrronium tosylate composition provided herein, or a pharmaceutically acceptable solvate or hydrate thereof. The amount of the glycopyrronium tosylate composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, administration of the same composition may be repeated and the administrations may be separated by at least 1 day, 2 days, 3 days, 5 days, 10 days, 15 days, 30 days, 45 days, 2 months, 75 days, 3 months, 6 months, or more. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, 6 months, or more.

Kits

Also provided are kits for use in methods of treatment of a disorder such as hyperhidrosis. The kits can include a compound or composition provided herein, a second agent or composition, and instructions providing information regarding usage for treating the disorder. Instructions may be provided in any form which can be conveniently accessed and/or received by a subject, including, but not limited to, printed form, floppy disc, CD, DVD, USB drive, website address, smartphone application, tablet application, wearable device application, text message, and message through a social media service.

In some embodiments, suitable packaging is provided. As used herein, "packaging" includes a material customarily used in a system and capable of holding within fixed limits a glycopyrronium tosylate composition provided herein and/or a second agent suitable for administration to a subject. Such materials include glass and plastic (e.g., polyethylene, polypropylene, and polycarbonate) bottles, vials, paper, plastic, wipes, and plastic-foil laminated envelopes and the like.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of Glycopyrronium Tosylate Using Methyl Tosylate as Methylation Agent Step 1: Preparation of Glycopyrrolate Base (Mixture of Erythro/Threo Base)

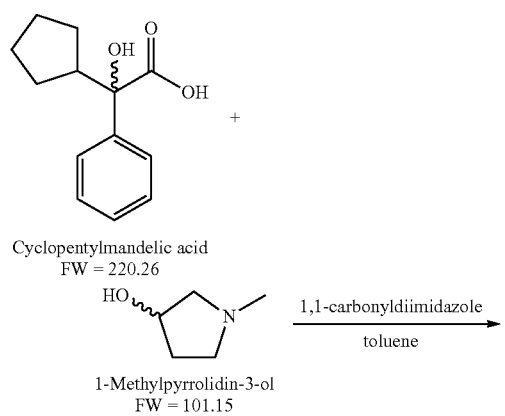

Cyclopentylmandelic acid
FW = 220.26

1-Methylpyrrolidin-3-ol
FW = 101.15

1,1-carbonyldiimidazole
toluene

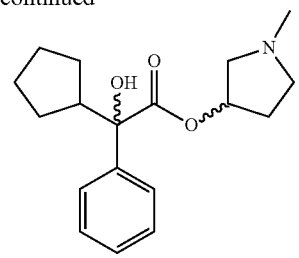

Glycopyrrolate base (mixture of four isomers)
FW = 303.40

Cyclopentylmandelic acid is activated by reaction under heating with 1,1-carbonyldiimidazole in toluene. N-methyl-3-pyridinol is added and stirred for at least five hours. After in-process testing to confirm completion of reaction, the mixture is cooled, washed with water, and the toluene solution concentrated to a mixture containing between 20-40% toluene and less than 4% residual cyclopentyl mandelic acid. This mixture is used directly in the next step.

Step 2: Preparation of Glycopyrrolate Base Threo Pair as 5-Nitroisophthalate Salt

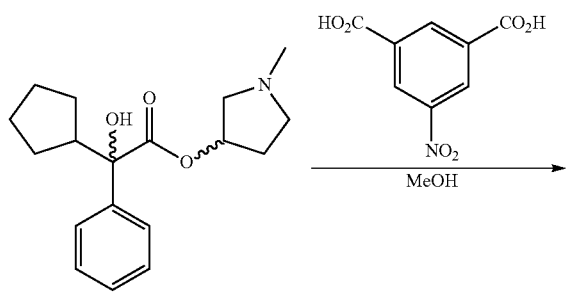

Glycopyrrolate base
(mixture of four isomers)
FW = 303.40

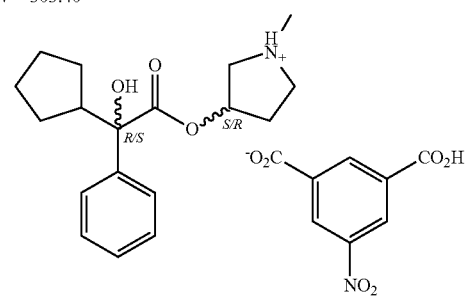

Glycopyrrolate base, 5-nitroisophthalate salt (threo pair)
FW = 514.53

This step effectively resolves the mixture of threo and erythro diastereomers of the free base intermediate to provide the threo pair at greater than 96%. The process relies on the significantly different solubilities of the 5-nitroisophthalate salts of the threo and erythro diastereomers of glycopyrrolate free base.

5-Nitroisophthalic acid (1 eq.) was dissolved in methanol (20 vol) at room temperature with moderate agitation. The glycopyrrolate base (1 eq.) obtained in Step 1 was then added. After crystallization was initiated, the mixture was stirred for an additional 4 hours at room temperature. The solids were then recovered in a filtration centrifuge and washed with methanol.

The crude product was then suspended in approximately 6 volumes of methanol. The suspension was stirred at approximately 65° C. for one hour, then cooled to 20° C. and stirred for an additional 4 hours. The product was again recovered in a filtration centrifuge, washed with methanol, spun dry at 1290 RPM for 15 minutes, and then discharged as wet glycopyrrolate 5-nitroisophthalate. The product was tested for identification, loss on drying, and melting point. The ratio of threo:erythro diastereomeric pairs was typically 96:4.

Step 3: Preparation of Threo-Glycopyrrolate Base

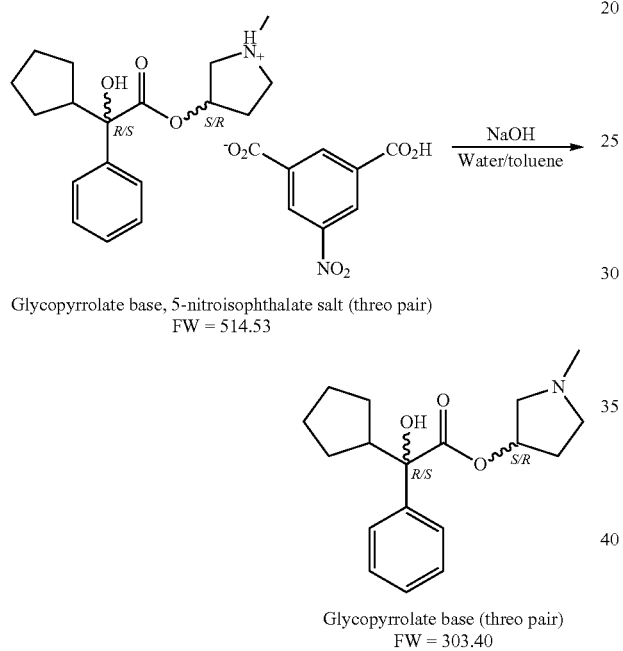

Glycopyrrolate base, 5-nitroisophthalate salt (threo pair)
FW = 514.53

Glycopyrrolate base (threo pair)
FW = 303.40

The threo-glycopyrrolate base was obtained by treatment of the wet 5-nitroisophthalate salt obtained in Step 2 with aqueous sodium hydroxide and toluene. A biphasic mixture was obtained in which the disodium salt of 5-nitroisophthalic acid resided in the aqueous layer and the threo-glycopyrrolate base was contained in the toluene layer.

The wet 5-nitroisophthalate salt of threo-glycopyrrolate base was dissolved in approximately 8 volumes of purified water at room temperature. Toluene (approximately 3 volumes) was added. With agitation, a slight excess of 30% aqueous sodium hydroxide was added and the mixture stirred for 15 minutes. A sample of the biphasic mixture was then taken and the pH of the aqueous layer verified to be in the range 11.5 to 12.5. In some instances, the pH was adjusted by addition of additional aqueous sodium hydroxide. The lower aqueous layer was removed by decanting and the upper toluene layer washed three times with purified water. The toluene was then removed by distillation under reduced pressure to yield the free base as an oil which was used directly in the next step.

Step 4: Preparation of Crude Glycopyrronium Tosylate

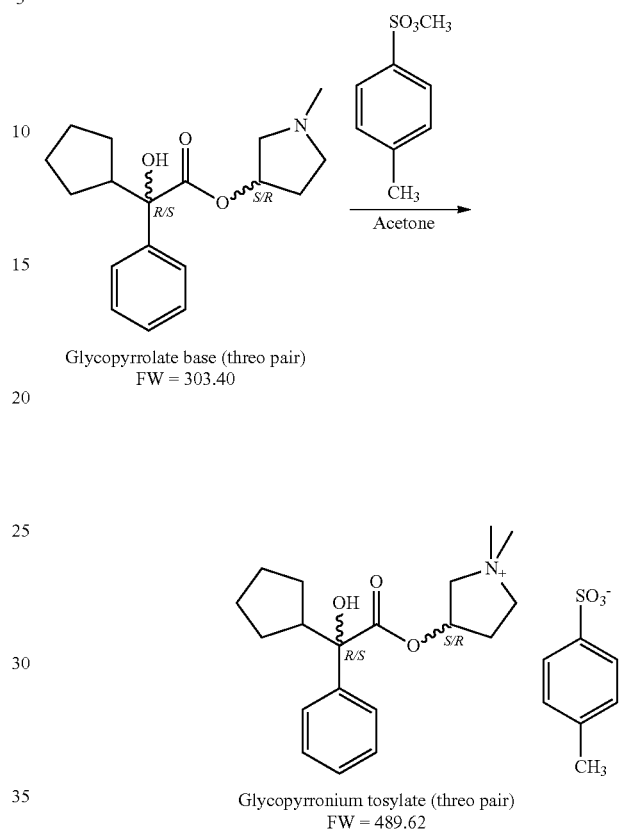

Glycopyrrolate base (threo pair)
FW = 303.40

Glycopyrronium tosylate (threo pair)
FW = 489.62

The threo-glycopyrrolate base obtained in the previous step was dissolved in four volumes of acetone and treated with 1.1 eq. of methyl-p-toluenesulfonate. The mixture was stirred for a minimum of three hours at room temperature, typically for about 12 hours at room temperature. Completion of the reaction was monitored by TLC until the remaining free base was not more than about 2%. The crude glycopyrronium tosylate was recovered using a filtration centrifuge and washed twice with a minimum of acetone. The wet cake obtained was dried under vacuum at 50° C. until the loss on drying was not more than 2.0%.

Step 5: Purification and Isolation of Threo-Glycopyrronium Tosylate

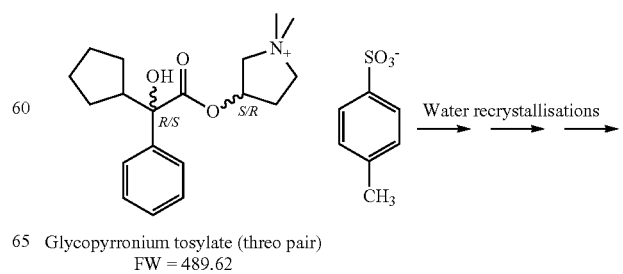

Glycopyrronium tosylate (threo pair)
FW = 489.62

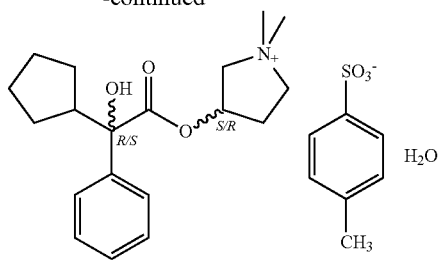

Glycopyrronium tosylate monohydrate (threo pair)
FW = 507.64

The purpose of the following purification steps was to reduce the content of the erythro isomer to the release limit of not more than 0.4%.

In the first purification step, the dried crude glycopyrronium tosylate was triturated in three volumes of purified water for five hours. The product was recovered using a filtration centrifuge and washed with 1 volume of cold (<10° C.) purified water. The wet cake was then dissolved in four volumes of purified water at 60° C. with agitation. The solution obtained was cooled to 35° C. and held until crystallization began (typically about 1 hour). The mixture was then cooled to 20° C. and agitated for a further 5 hours. The product was then recovered using a filtration centrifuge and washed with 1 volume of cold (<10° C.) purified water. Finally, the product was recrystallized a second time in a similar fashion from 3 volumes of purified water with polish filtration of the 60° C. solution prior to cooling.

At each step of the purification process, the wet cake was sampled and analyzed for loss on drying and erythro isomer content. The erythro isomer limit of 0.4% was typically met after the second crystallization, however additional recrystallization steps were performed as required until the erythro isomer limit was met. The product was tray dried at not more than 40° C. without vacuum for a minimum of 8 hours until the water content met the release criteria of 2.5%-4.0%.

Elemental analysis: C, 61.59%; H, 7.27%; N, 2.80%; S, 6.31%. The molecular formula of glycopyrronium tosylate monohydrate is $C_{26}H_{37}NO_7S$, which corresponds to: C, 61.51%; H, 7.35%; N, 2.76%; and S, 6.32%.

$^1$H NMR (DMSO-$d_6$): δ=1.15 (m, 1H), 1.20 (m, 1H), 1.40 (m, 1H), 1.50 (m, 2H), 1.60 (m, 3H), 2.05 (m, 1H), 2.30 (s, 3H), 2.65 (m, 1H), 2.90 (m, 1H), 3.05 (s, 3H), 3.15 (s, 3H), 3.50 (m, 1H), 3.60 (d, 1H), 3.70 (m, 1H), 3.80 (dd, 1H), 5.37 (m, 1H), 5.82 (s, 1H), 7.10 (d, 2H), 7.27 (t, 1H), 7.35 (7.47 (d, 2H), 7.59 (d, 2H).

ESI-MS(+): m/z 318 (glycopyrronium); ESI-MS(−): m/z 171 (tosylate).

IR (ATR): 681-907 cm−1 (C—H arom.); 1012, 1036 cm$^{-1}$ (C—N, C—O, C=S str); 1195 cm$^{-1}$ (C—O ester str); 1320, 1361, 1445 cm$^{-1}$ (S=O); 1734 cm$^{-1}$ (C=O ester); 2868-3033 cm$^{-1}$ (C—H aliph); 3419, 3569 cm$^{-1}$ (O—H str).

Impurity Profile

The measured impurities were consistent with those of the United States Pharmacopeia monograph of Glycopyrrolate, the bromide salt. They are: Impurity A (5-nitroisophthalic acid), believed to be from the chiral resolution of the glycopyrrolate base intermediate; Impurity B (glycopyrrolate base intermediate); and Impurity C (cyclopentylmandelic acid) which is used in the first step of the synthesis, and is also believed to be the primary degradation product. No other impurities were observed in the batches or forced degradation studies. All batches have contained very low levels of total impurities and easily met the limit of 0.15%.

An additional potential impurity is methyl tosylate used in the quaternization step. Methyl tosylate is believed to be unstable in aqueous medium and effectively cleared by the final crystallization steps. Methyl tosylate levels are consistently not detected, at a limit of detection of 2.25 ppm.

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A method of producing glycopyrronium tosylate comprising:
   (a) contacting glycopyrrolate base with methyl tosylate to produce glycopyrronium tosylate:

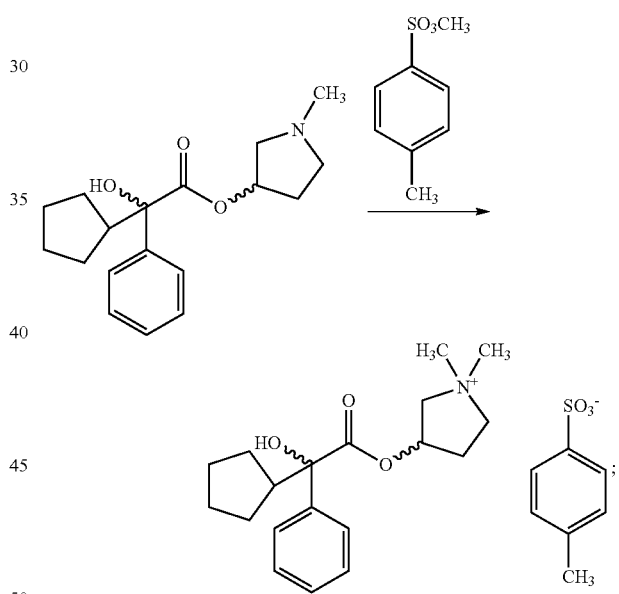

and
   (b) purifying the glycopyrronium tosylate obtained in step (a) by one or more crystallizations in an aqueous solvent to obtain a purified glycopyrronium tosylate; wherein the aqueous solvent consists essentially of water.

2. The method of claim 1, wherein the glycopyrrolate base contacted with methyl tosylate is contacted with an organic solvent.

3. The method of claim 2, wherein the organic solvent is acetone or ethyl acetate.

4. The method of claim 1, wherein the aqueous solvent consists of water.

5. The method of claim 4, wherein the purified glycopyrronium tosylate is in the form of glycopyrronium tosylate monohydrate.

6. The method of claim 1, wherein in the purified glycopyrronium tosylate of step (b) the threo-glycopyrronium tosylate is at least 99.5% of the total glycopyrronium tosylate in the mixture and the erythro-glycopyrronium tosylate is less than 0.5% of the total glycopyrronium tosylate in the mixture.

7. The method of claim 1, wherein in the purified glycopyrronium tosylate of step (b) the threo-glycopyrronium tosylate is at least 99.6% of the total glycopyrronium tosylate in the mixture and the erythro-glycopyrronium tosylate is less than 0.4% of the total glycopyrronium tosylate in the mixture.

8. The method of claim 1, wherein the glycopyrrolate base is produced by contacting a glycopyrrolate base, 5-nitroisophthalate salt with an inorganic base to form the glycopyrrolate base:

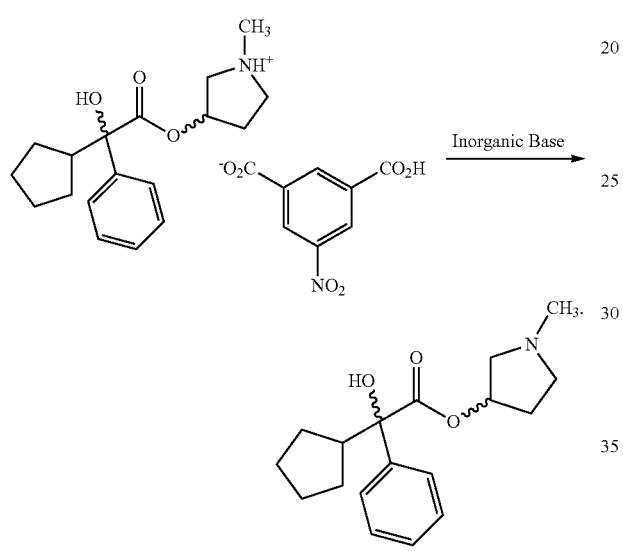

9. The method of claim 8, wherein the glycopyrrolate base, 5-nitroisophthalate salt and inorganic base are contacted with an organic solvent.

10. The method of claim 9, wherein the organic solvent is toluene.

11. The method of claim 8, wherein the inorganic base is aqueous sodium hydroxide.

12. The method of claim 8, wherein the glycopyrrolate base is produced as a mixture of threo-glycopyrrolate base and erythro-glycopyrrolate base, and the threo-glycopyrrolate base is at least 95% of the total glycopyrrolate base produced and the erythro-glycopyrrolate base is less than 5% of the total glycopyrrolate base produced.

13. The method of claim 12, wherein the threo-glycopyrrolate base is at least 96% of the total glycopyrrolate base produced and the erythro-glycopyrrolate base is less than 4% of the total glycopyrrolate base produced.

14. The method of claim 12, wherein the threo-glycopyrrolate base is at least 97% of the total glycopyrrolate base produced and the erythro-glycopyrrolate base is less than 3% of the total glycopyrrolate base produced.

15. The method of claim 8, wherein the glycopyrrolate base, 5-nitroisophthalate salt is produced by contacting a glycopyrrolate base with 5-nitroisophthalic acid to form the glycopyrrolate base, 5-nitroisophthalate salt:

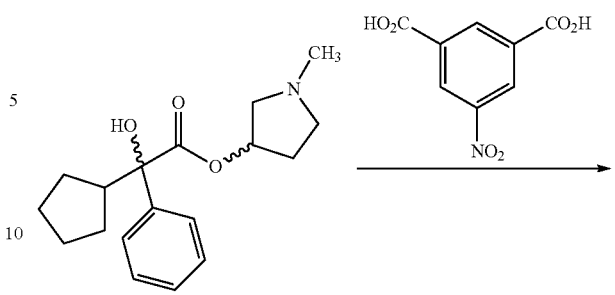

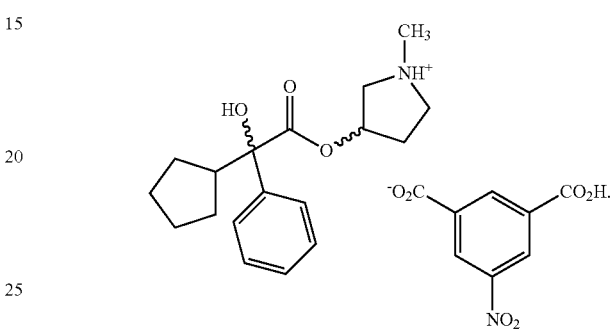

16. The method of claim 15, wherein the glycopyrrolate base and 5-nitroisophthalic acid are contacted with methanol.

17. The method of claim 2, wherein the organic solvent is ethyl acetate.

18. The method of claim 1, wherein the level of total impurity is not more than 0.15%.

19. A method of producing glycopyrronium tosylate comprising:

(i) contacting cyclopentylmandelic acid with 1-methyl-pyrrolidin-3-ol to form glycopyrrolate base:

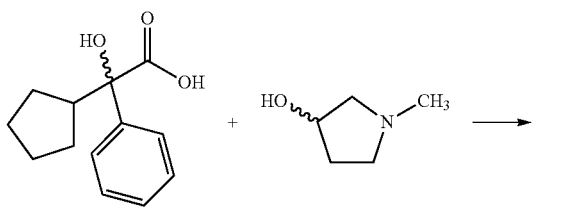

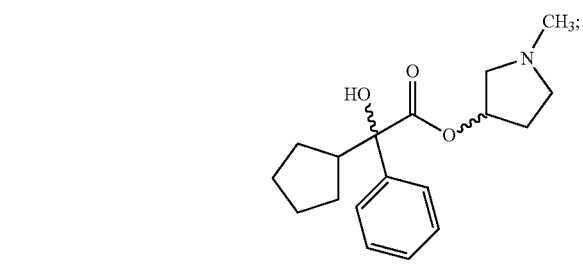

(ii) contacting the glycopyrrolate base with 5-nitroisophthalic acid to form glycopyrrolate base, 5-nitroisophthalate salt:

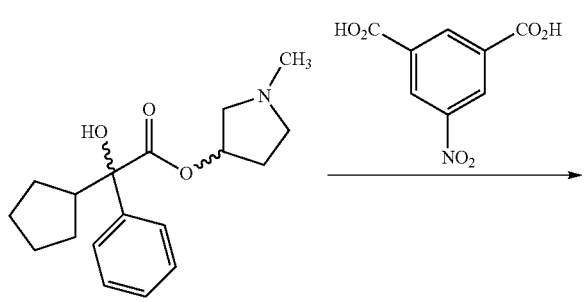

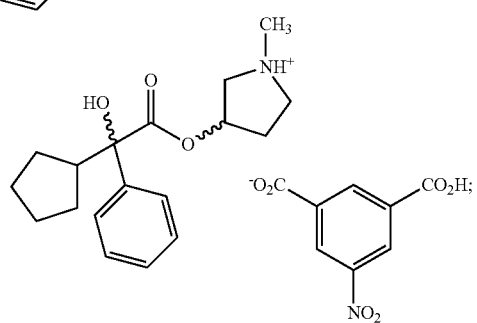

(iii) contacting the glycopyrrolate base, 5-nitroisophthalate salt with an inorganic base to form glycopyrrolate base:

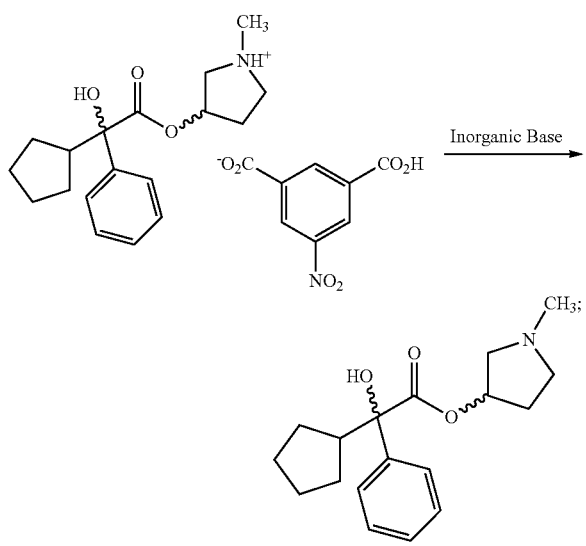

(iv) contacting the glycopyrrolate base with methyl tosylate to produce glycopyrronium tosylate:

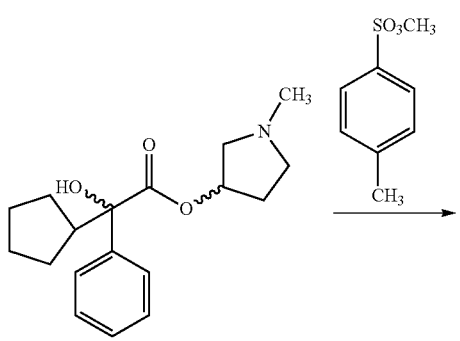

-continued

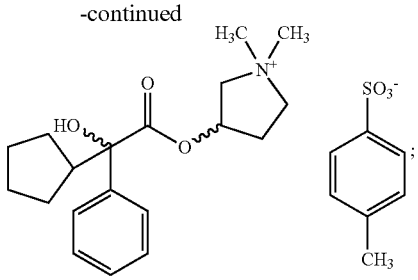

and (v) purifying the glycopyrronium tosylate obtained in step (iv) by one or more crystallizations in an aqueous solvent to obtain a purified glycopyrronium tosylate; wherein the aqueous solvent consists essentially of water.

20. The method of claim 19, wherein the aqueous solvent in step (v) consists of water.

21. The method of claim 1, wherein the step (b) is purifying the glycopyrronium tosylate obtained in step (a) by at least two crystallizations in the aqueous solvent to obtain a purified glycopyrronium tosylate;
wherein the purified glycopyrronium tosylate is a mixture of threo-glycopyrronium tosylate and erythro-glycopyrronium tosylate, and the threo-glycopyrronium tosylate is at least 99.6% of the total glycopyrronium tosylate in the mixture and the erythro-glycopyrronium tosylate is less than 0.4% of the total glycopyrronium tosylate in the mixture.

22. The method of claim 1, wherein the step (b) is purifying the glycopyrronium tosylate obtained in step (a) by at least two crystallizations in the aqueous solvent to obtain a purified glycopyrronium tosylate; wherein the aqueous solvent consists of water;
wherein the purified glycopyrronium tosylate is a mixture of threo-glycopyrronium tosylate and erythro-glycopyrronium tosylate, and the threo-glycopyrronium tosylate is at least 99.6% of the total glycopyrronium tosylate in the mixture and the erythro-glycopyrronium tosylate is less than 0.4% of the total glycopyrronium tosylate in the mixture.

23. The method of claim 19, wherein the step (v) is purifying the glycopyrronium tosylate obtained in step (iv) by at least two crystallizations in the aqueous solvent to obtain a purified glycopyrronium tosylate;
wherein the purified glycopyrronium tosylate is a mixture of threo-glycopyrronium tosylate and erythro-glycopyrronium tosylate, and the threo-glycopyrronium tosylate is at least 99.6% of the total glycopyrronium tosylate in the mixture and the erythro-glycopyrronium tosylate is less than 0.4% of the total glycopyrronium tosylate in the mixture.

24. The method of claim 19, wherein the step (v) is purifying the glycopyrronium tosylate obtained in step (iv) by at least two crystallizations in the aqueous solvent to obtain a purified glycopyrronium tosylate; wherein the aqueous solvent consists of water;
wherein the purified glycopyrronium tosylate is a mixture of threo-glycopyrronium tosylate and erythro-glycopyrronium tosylate, and the threo-glycopyrronium tosylate is at least 99.6% of the total glycopyrronium tosylate in the mixture and the erythro-glycopyrronium tosylate is less than 0.4% of the total glycopyrronium tosylate in the mixture.

25. A method of producing glycopyrronium tosylate comprising:

(i) contacting glycopyrrolate base with 5-nitroisophthalic acid to form a glycopyrrolate base, 5-nitroisophthalate salt:

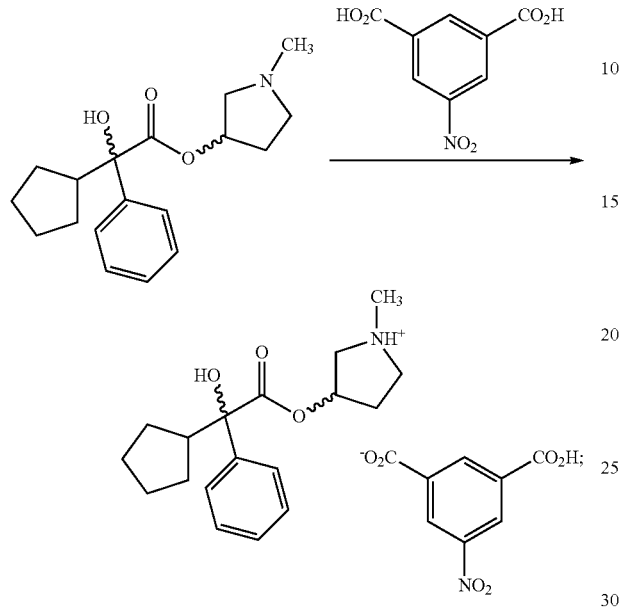

(ii) contacting the glycopyrrolate base, 5-nitroisophthalate salt with an inorganic base to form glycopyrrolate base:

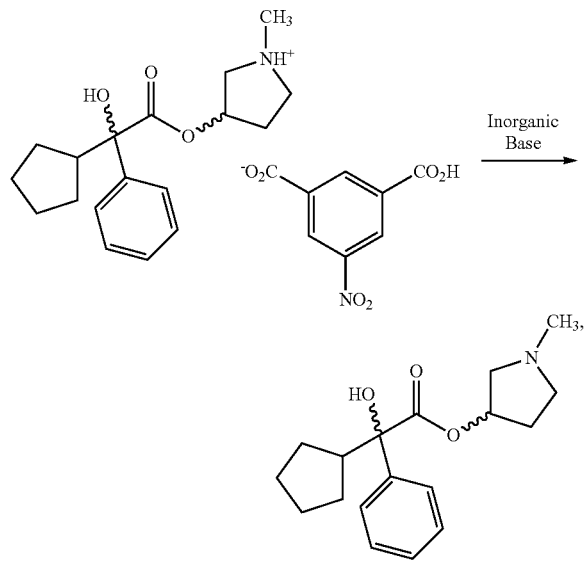

wherein the glycopyrrolate base is a mixture of threo-glycopyrrolate base and erythro-glycopyrrolate base, and the threo-glycopyrrolate base is 95% to 97% of the total glycopyrrolate base produced and the erythro-glycopyrrolate base is 5% to 3% of the total glycopyrrolate base produced;

(iii) contacting the glycopyrrolate base with methyl tosylate to produce glycopyrronium tosylate:

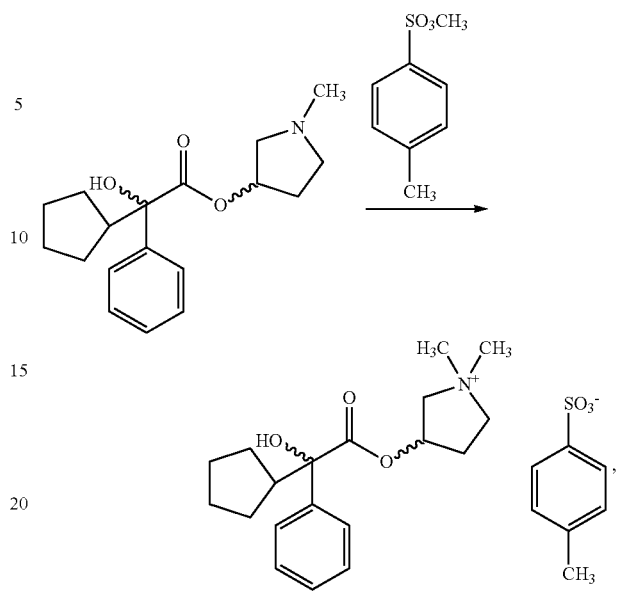

wherein the glycopyrronium tosylate is a mixture of threo-glycopyrronium tosylate and erythro-glycopyrronium tosylate, wherein the threo-glycopyrronium tosylate is 95% to 97% of the total glycopyrronium tosylate in the mixture and the erythro-glycopyrronium tosylate is 5% to 3% of the total glycopyrronium tosylate in the mixture; and (iv) purifying the glycopyrronium tosylate in step (iii) by one or more crystallizations in an aqueous solvent to obtain a purified glycopyrronium tosylate;

wherein the purified glycopyrronium tosylate is a mixture of threo-glycopyrronium tosylate and erythro-glycopyrronium tosylate, wherein the threo-glycopyrronium tosylate is at least 99% of the total glycopyrronium tosylate in the mixture and the erythro-glycopyrronium tosylate is less than 1% of the total glycopyrronium tosylate in the mixture.

26. The method of claim 25, wherein in the purified glycopyrronium tosylate of step (iv) the threo-glycopyrronium tosylate is at least 99.5% of the total glycopyrronium tosylate in the mixture and the erythro-glycopyrronium tosylate is less than 0.5% of the total glycopyrronium tosylate in the mixture.

27. The method of claim 25, wherein in the purified glycopyrronium tosylate of step (iv) the threo-glycopyrronium tosylate is at least 99.6% of the total glycopyrronium tosylate in the mixture and the erythro-glycopyrronium tosylate is less than 0.4% of the total glycopyrronium tosylate in the mixture.

28. The method of claim 1, wherein in the purified glycopyrronium tosylate of step (b) the threo-glycopyrronium tosylate is at least 99% of the total glycopyrronium tosylate in the mixture and the erythro-glycopyrronium tosylate is less than 1% of the total glycopyrronium tosylate in the mixture.

29. The method of claim 19, wherein in the purified glycopyrronium tosylate of step (v) the threo-glycopyrronium tosylate is at least 99% of the total glycopyrronium tosylate in the mixture and the erythro-glycopyrronium tosylate is less than 1% of the total glycopyrronium tosylate in the mixture.

* * * * *